(12) United States Patent
Jegorov et al.

(10) Patent No.: US 8,067,421 B2
(45) Date of Patent: Nov. 29, 2011

(54) POLYMORPHIC FORMS OF IMATINIB MESYLATE AND PROCESSES FOR PREPARATION OF NOVEL CRYSTALLINE FORMS AS WELL AS AMORPHOUS AND FORM α

(75) Inventors: Alexandr Jegorov, Dobrá Voda (CZ); Miloslav Chudík, Karviná (CZ); Judith Aronhime, Rehovot (IL); Aleš Gavenda, Ostrava (CZ); Jiří Faustmann, Opava (CZ)

(73) Assignee: Sicor Inc., Irvine, CA (US)

( * ) Notice: Subject to any disclaimer, the term of this patent is extended or adjusted under 35 U.S.C. 154(b) by 1193 days.

(21) Appl. No.: 11/796,573

(22) Filed: Apr. 27, 2007

(65) Prior Publication Data

US 2008/0090833 A1    Apr. 17, 2008

Related U.S. Application Data

(60) Provisional application No. 60/796,253, filed on Apr. 27, 2006, provisional application No. 60/818,916, filed on Jul. 5, 2006, provisional application No. 60/837,420, filed on Aug. 10, 2006, provisional application No. 60/847,631, filed on Sep. 26, 2006, provisional application No. 60/852,349, filed on Oct. 16, 2006, provisional application No. 60/854,221, filed on Oct. 24, 2006, provisional application No. 60/861,825, filed on Nov. 29, 2006, provisional application No. 60/918,178, filed on Mar. 14, 2007, provisional application No. 60/922,034, filed on Apr. 4, 2007, provisional application No. 60/923,440, filed on Apr. 12, 2007.

(51) Int. Cl.
   *A01N 43/54* (2006.01)
   *C07D 239/42* (2006.01)

(52) U.S. Cl. ......... 514/256; 544/242; 544/336; 544/357

(58) Field of Classification Search .................. 544/336, 544/357, 242; 514/247, 252.1, 256
See application file for complete search history.

(56) References Cited

U.S. PATENT DOCUMENTS

| | | | |
|---|---|---|---|
| 5,521,184 | A | 5/1996 | Zimmermann |
| 6,894,051 | B1 | 5/2005 | Zimmermann et al. |
| 7,081,532 | B2 | 7/2006 | Buerger et al. |
| 7,550,591 | B2 | 6/2009 | Xing et al. |
| 2004/0248918 | A1 | 12/2004 | Kim et al. |
| 2006/0030568 | A1 | 2/2006 | Zimmermann et al. |
| 2006/0149061 | A1 | 7/2006 | Anli et al. |
| 2006/0223816 | A1 | 10/2006 | Adin et al. |
| 2006/0223817 | A1 | 10/2006 | Adin et al. |

FOREIGN PATENT DOCUMENTS

| | | | |
|---|---|---|---|
| WO | WO 99/03854 | * | 1/1999 |
| WO | WO-99/03854 A1 | | 1/1999 |
| WO | WO-03/066613 A1 | | 8/2003 |
| WO | WO-2004/074502 A2 | | 9/2004 |
| WO | WO 2004/106326 | * | 12/2004 |
| WO | WO-2004/106326 A1 | | 12/2004 |
| WO | WO-2004/108699 A1 | | 12/2004 |
| WO | WO-2005/077933 A1 | | 8/2005 |
| WO | WO-2005/095379 A2 | | 10/2005 |
| WO | WO-2006/024863 A1 | | 3/2006 |
| WO | WO-2006/048890 A1 | | 5/2006 |
| WO | WO-2006/054314 A1 | | 5/2006 |
| WO | WO-2006/071130 A2 | | 7/2006 |
| WO | WO-2007/023182 A1 | | 3/2007 |
| WO | WO-2009/080366 A1 | | 7/2009 |

OTHER PUBLICATIONS

ICH Harmonised Tripartite Guideline, "Good Manufacturing Practice Guide for Active Pharmaceutical Ingredients", Q7A, Current Step 4 Version, Nov. 10, 2000.
Strobel, Howard A., et al., "Chemical Instrumentation: A Systematic Approach", 3rd edition, Wiley & Sons, New York, 1989, p. 953.

* cited by examiner

*Primary Examiner* — Paul V. Ward
(74) *Attorney, Agent, or Firm* — Kenyon & Kenyon LLP

(57) ABSTRACT

Solvates and crystalline forms of imatinib mesylate are described. Further, methods for preparing such solvates and crystalline forms of imatinib mesylate are described.

23 Claims, 20 Drawing Sheets

A powder X-ray diffraction pattern for imatinib mesylate Form IV.

A solid-state $^{13}$C NMR spectrum of imatinib mesylate Form IV in the 100–180 ppm range.

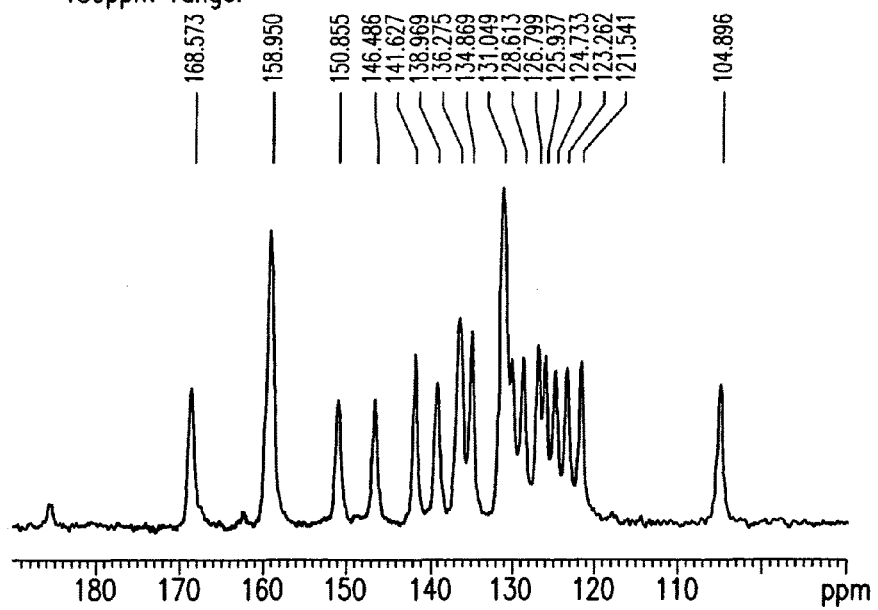
FIG.11 A solid-state $^{13}$C NMR spectrum of imatinib mesylate Form VII in the 100-180ppm range.
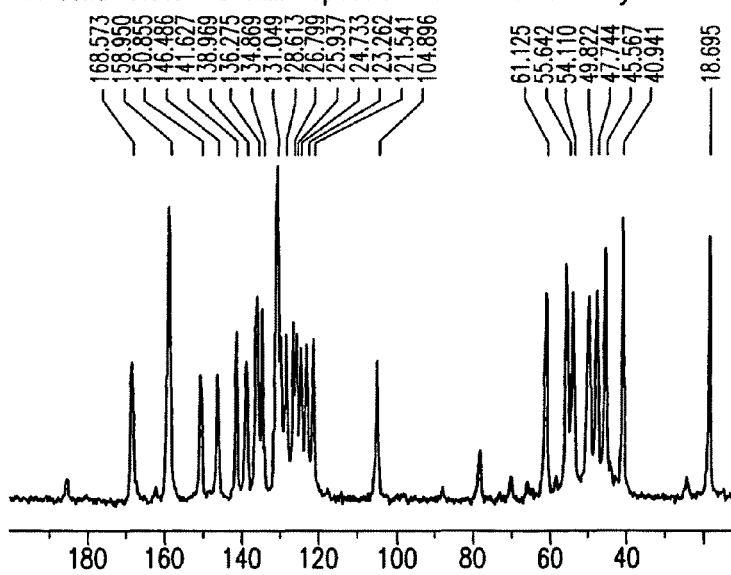
FIG.12 A solid-state $^{13}$C NMR spectrum of imatinib mesylate Form VII.

A powder X-ray diffraction pattern for imatinib mesylate Form XVI.

A powder X-ray diffraction pattern for amorphous imatinib mesylate.

POLYMORPHIC FORMS OF IMATINIB MESYLATE AND PROCESSES FOR PREPARATION OF NOVEL CRYSTALLINE FORMS AS WELL AS AMORPHOUS AND FORM α

CROSS REFERENCE TO RELATED APPLICATIONS

The present application claims the benefit of the following U.S. Provisional Patent Application Nos. 60/796,253, filed Apr. 27, 2006; 60/818,916, filed Jul. 5, 2006; 60/837,420, filed Aug. 10, 2006; 60/847,631, filed Sep. 26, 2006; 60/852,349, filed Oct. 16, 2006; 60/854,221, filed Oct. 24, 2006; 60/861,825, filed Nov. 29, 20006; 60/918,178, filed Mar. 14, 2007; 60/922,034, filed Apr. 4, 2007; and Ser. No. 60/923,440, filed Apr. 12, 2007. The contents of these applications are incorporated herein by reference.

FIELD OF THE INVENTION

The present invention encompasses forms of imatinib mesylate as well as processes for the preparation thereof.

BACKGROUND OF THE INVENTION

Imatinib mesylate, 4-(4-methylpiperazin, 1-ylmethyl)-N-[4-methyl-3-[(4-pyrinin-3-yl)pyrimidin-2-yloamino]phenyl]benzamide mesylate, a compound having the chemical structure,

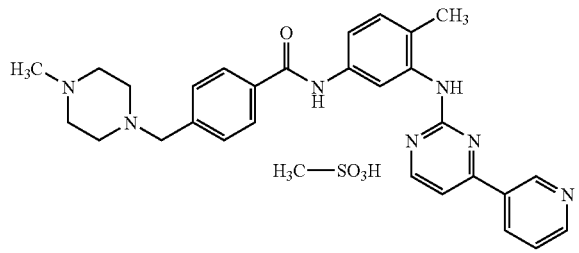

Imatinib is a protein-tyrosine kinase inhibitor, especially useful in the treatment of various types of cancer and can also be used for the treatment of atherosclerosis, thrombosis, restenosis, or fibrosis. Thus imatinib can also be used for the treatment of non-malignant diseases. Imatinib is usually administered orally in the form of a suitable salt, e.g., in the form of imatinib mesylate.

The present invention relates to the solid-state physical properties of imatinib mesylate. These properties can be influenced by controlling the conditions under which imatinib mesylate is obtained in solid form. Solid-state physical properties include, for example, the flow-ability of the milled solid. Flow-ability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid-state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid-state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetric (DSC) and can be used to distinguish some polymorphic forms from others. A particular polymorphic form may also give rise to distinct spectroscopic properties that may be detectable by powder X-ray crystallography, solid-state $^{13}$C NMR spectrometry and infrared spectrometry.

The present invention also relates to solvates of imatinib mesylate. When a substance crystallizes out of solution, it may trap molecules of solvent at regular intervals in the crystal lattice. Solvation also affects utilitarian physical properties of the solid-state like flowability, dissolution rate, and makes it possible to prepare new forms by the desolvation of solvates.

One of the most important physical properties of a pharmaceutical compound, which can form polymorphs or solvates, is its solubility in aqueous solution, particularly the solubility in gastric juices of a patient. Other important properties relate to the ease of processing the form into pharmaceutical dosages, as the tendency of a powdered or granulated form to flow and the surface properties that determine whether crystals of the form will adhere to each other when compacted into a tablet.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

There is a need in the art for new polymorphs of imatinib mesylate and processes for the preparation of imatinib mesylate forms.

SUMMARY OF THE INVENTION

In one embodiment, the present invention provides imatinib mesylate solvates.

In another embodiment, the present invention provides imatinib mesylate solvates with solvents selected from the group consisting of: aliphatic alcohols, ethers, dioxolane, nitromethane and acetic acid.

In one embodiment, the present invention provides crystalline imatinib mesylate characterized by data selected from the group consisting of: a powder XRD pattern with peaks at about 8.1, 9.7, 17.0, 20.1, and 21.5±0.2 degrees two-theta; a powder XRD pattern with peaks at about 8.1, 9.7, 13.2, 16.2, and 17.0±0.2 degrees two-theta; a powder XRD pattern having peaks at: 8.1, 9.7, 16.2, 17.0 and 21.5±0.2 degrees two-theta; a PXRD pattern having at least five peaks selected from the list consisting of: 8.1, 9.7, 13.2, 14.3, 16.2, 17.0, 24.1, 24.8, 25.8, 26.6, 28.9, 30.3±0.2 degrees two-theta; a powder XRD pattern as depicted in FIG. 1; a solid-state $^{13}$C NMR spectrum with peaks at about 162.3, 160.9, 157.1±0.2 ppm; a solid-state $^{13}$C NMR spectrum having chemical shifts differences between the signal exhibiting the lowest chemical shift and another in the chemical shift range of 100 to 180 ppm of about 56.1, 54.7 and 50.9±0.1 ppm, a solid state $^{13}$C NMR spectrum depicted in FIG. 2, and a and a solid-state $^{13}$C NMR spectrum substantially as depicted in FIG. 3.

In one embodiment, the present invention encompasses a process for preparing the above imatinib mesylate comprising: providing a solution of imatinib mesylate comprising imatinib mesylate and ethanol; cooling to a temperature of about 10° C. to about −50° C. to obtain a precipitate of the said crystalline form; and recovering the said crystalline form.

In another embodiment, the present invention provides crystalline imatinib mesylate characterized by data selected from the group consisting of: a powder XRD pattern with peaks at about 9.9, 11.7, 13.3, 16.6, and 22.1±0.2 degrees two-theta; a powder XRD pattern with peaks at about 9.9, 11.7, 13.3, and 16.6±0.2 degrees two-theta; a PXRD pattern having peaks at 5.6, 9.9, 11.7, 13.3, 16.6, and 18.5±0.2 degrees two-theta; a PXRD pattern having at least five peaks selected from the list of 5.6, 9.9, 11.7, 13.3, 16.6, 18.5, 22.1, 24.0, 26.2, 26.9±0.2 degrees two-theta; a PXRD pattern depicted in the FIG. 4; a solid-state $^{13}$C NMR spectrum with peaks at about 162.8, 161.5, 158.5±0.2 ppm; a solid-state $^{13}$C NMR spectrum having chemical shifts differences between the signal exhibiting the lowest chemical shift and another in the chemical shift range of 100 to 180 ppm of about 53.9, 52.6 and 49.6±0.1 ppm, a solid state $^{13}$C NMR depicted in FIG. 5, and a solid state $^{13}$C NMR spectrum depicted in FIG. 6.

In another embodiment, the present invention provides a process for preparing the above crystalline imatinib mesylate comprising drying crystalline Form VI at a temperature of about room temperature to about 90° C.

In yet another embodiment, the present invention provides crystalline imatinib mesylate characterized by data selected from the group consisting of: a powder XRD pattern with peaks at about 16.6, 17.1, 18.6, 20.4, and 21.2±0.2 degrees two-theta; a powder XRD pattern with peaks at about 8.5, 9.2, 16.6, and 17.1±0.2 degrees two-theta; a powder XRD pattern having peaks at: 8.5, 16.6, 17.1, and 18.6±0.2 degrees two-theta; a PXRD pattern having at least five peaks selected from the list of 8.5, 9.2, 16.6, 17.1, 18.6, 22.2, 24.6, 25.4±0.2 degrees two-theta; a PXRD pattern depicted in FIG. 7; a solid-state $^{13}$C NMR spectrum having peaks at about 162.0, 160.5 and 156.9, 153.2±0.2 ppm; a solid-state $^{13}$C NMR spectrum having chemical shift differences between the signal exhibiting the lowest chemical shift and another in the chemical shift range of 100 to 180 ppm of about 55.8, 54.4, 50.7 and 47.0±0.1 ppm; a solid state $^{13}$C NMR spectrum depicted in FIG. 8, and a solid-state $^{13}$C NMR spectrum depicted in FIG. 9.

In one embodiment, the present invention further encompasses a process for preparing the above crystalline imatinib mesylate comprising: crystallizing imatinib mesylate from a solution of imatinib mesylate in aqueous 1,3-dioxolane to obtain a precipitate; and recovering the crystalline imatinib mesylate.

In one embodiment, the present invention provides crystalline imatinib mesylate characterized by data selected from the group consisting of: a powder XRD pattern with peaks at about 10.1, 13.4, 17.7, 20.6, 24.6±0.2 degrees two-theta; a powder XRD pattern with peaks at about 10.1, 13.4, 15.0, 16.2, and 17.7±0.2 degrees two-theta; a powder XRD pattern having at least five peaks selected from the list consisting of: 8.2, 10.1, 13.4, 15.0, 16.2, 17.7, 19.4, 24.6, 28.5, 29.7±0.2 degrees two-theta; a PXRD pattern depicted in the PXRD pattern in FIG. 10; a solid-state $^{13}$C NMR spectrum having peaks at about 159.0, 150.9 and 146.5±0.2 ppm; a solid-state $^{13}$C NMR spectrum having chemical shift differences between the signal exhibiting the lowest chemical shift and another in the chemical shift range of 100 to 180 ppm of about 54.1, 46.0 and 41.6±0.1 ppm; a solid state $^{13}$C NMR spectrum depicted in FIG. 11, and a and a solid-state $^{13}$C NMR spectrum depicted in FIG. 12.

In another embodiment, the present invention provides crystalline imatinib mesylate characterized by data selected from the group consisting of: a powder XRD pattern with peaks at about 8.5, 9.3, 15.8, 17.1, and 21.4±0.2 degrees two-theta; a powder XRD pattern with peaks at about 8.5, 9.3, 15.8, and 17.1±0.2 degrees two-theta; a powder XRD pattern having peaks at: 8.5, 9.3, 15.8, 17.1 and 18.5±0.2 degrees two-theta; a PXRD pattern having at least five peaks selected from the list consisting of: 8.5, 9.3, 13.2, 13.8, 14.6, 15.8, 16.6, 17.1, 18.5, 19.4, 21.4, 22.3±0.2 degrees two-theta; a powder XRD pattern depicted in FIG. 13; a solid-state $^{13}$C NMR spectrum having peaks at about 162.2, 161.0, 157.1±0.2 ppm; a solid-state $^{13}$C NMR spectrum having chemical shift differences between the signal exhibiting the lowest chemical shift and another in the chemical shift range of 100 to 180 ppm of about 55.5, 54.3 and 50.4±0.1 ppm; a solid-state $^{13}$C NMR spectrum depicted in FIG. 14, and a solid-state $^{13}$C NMR spectrum depicted in FIG. 15.

In yet another embodiment, the present invention provides crystalline imatinib mesylate, characterized by data selected from the group consisting of: a powder XRD pattern with peaks at about 10.4, 14.8, 18.2, and 24.7±0.2 degrees two-theta; a powder XRD pattern depicted in FIG. 16; a solid-state $^{13}$C NMR spectrum with peaks at about 157.9, 151.3 and 148.3±0.2 ppm; a solid-state $^{13}$C NMR spectrum having differences in chemical shifts between the signal exhibiting the lowest chemical shift and another in the chemical shift range of 100 to 180 ppm of about 45.6, 39.0, 36.0±0.1 ppm; a solid-state $^{13}$C NMR spectrum depicted in FIG. 17; and a solid-state $^{13}$C NMR spectrum depicted in FIG. 18.

In one embodiment, the present invention provides crystalline imatinib mesylate characterised by data selected from the group consisting of: a powder XRD pattern with peaks at about 6.0, 8.6, 11.4, 14.2, 18.3±0.2 degrees two-theta; a powder XRD pattern having peaks at: 6.0, 8.6, 10.2, 11.4, 14.2, ±0.2 degrees two-theta; a PXRD pattern having at least five peaks selected from the list consisting of: 6.0, 8.6, 10.2, 11.4, 14.2, 17.8, 18.3, 21.6, 22.4, 23.6, 24.8±0.2 degrees two-theta; a powder XRD pattern depicted in FIG. 19; a solid-state $^{13}$C NMR spectrum with peaks at about 159.9, 158.2 and 153.4±0.2 ppm; a solid-state $^{13}$C NMR spectrum having chemical shift differences between the signal exhibiting the lowest chemical shift and another in the chemical shift range of 100 to 180 ppm of about 51.5, 49.8, and 45.0±0.1 ppm; a solid-state $^{13}$C NMR spectrum depicted in FIG. 20; and a solid-state $^{13}$C NMR spectrum depicted in FIG. 21.

In another embodiment, the present invention provides a process for preparing the above crystalline imatinib mesylate by a process comprising: maintaining imatinib mesylate form IV at a temperature of about 20° C. to about 30° C.

In another embodiment, the present invention provides process for preparing the above crystalline Imatinib mesylate comprising providing a solution of imatinib mesylate and a mixture of water and ethanol; and precipitating by maintaining the solution at a temperature of about 0° C. to about −30° C., In another embodiment, the present invention further encompasses a process for preparing the above crystalline Imatinib mesylate comprising providing a suspension of imatinib mesylate form V and ethanol.

In another embodiment, the present invention provides crystalline imatinib mesylate characterised by data selected from a group consisting of: a powder XRD pattern with peaks at about 10.4, 11.8, 14.8 and 21.2±0.2 degrees two-theta; a powder XRD pattern with peaks at about 10.4, 14.8, 18.6, and 21.2±0.2 degrees two-theta; a powder XRD pattern having peaks at: 10.4, 11.8, 14.8, and 18.6±0.2 degrees two-theta; a powder XRD pattern having at least five peaks selected from the list consisting of: 10.4, 11.2, 11.8, 14.8, 18.6, 21.9, 22.6, 24.9±0.2 degrees two-theta; and a PXRD pattern depicted in FIG. 22.

In one embodiment, the present invention provides crystalline imatinib mesylate characterized by data selected from a group consisting of: a powder XRD pattern with peaks at about 10.0, 10.8, 11.9, 12.6 and 18.8±0.2 degrees two-theta; a powder XRD pattern with peaks at about 10.0, 10.8, 12.6 and 14.3±0.2 degrees two-theta, a powder XRD pattern having peaks at: 10.0, 10.8, 12.0, 12.6, and 16.7±0.2 degrees two-theta; a powder XRD pattern having at least five peaks selected from the list consisting of: 10.0, 10.8, 11.9, 12.6, 14.3, 15.6, 17.1, 18.8, 22.7, 23.6, 24.4±0.2 degrees two-theta; and a PXRD pattern depicted in FIG. 24.

In another embodiment, the present invention provides crystalline imatinib mesylate characterised by data selected from a group consisting of: a powder XRD pattern with peaks at about 9.7, 16.0, 17.0, 19.5, 21.1, 25.2±0.2 degrees two-theta; PXRD peaks at: 8.0, 9.7, 21.1 and 25.2±0.2 degrees two-theta; and PXRD pattern depicted in FIG. 25.

In yet another embodiment, the present invention provides crystalline imatinib mesylate characterized by data selected from the group consisting of: a powder XRD pattern with peaks at about 6.5, 8.6, 14.1, 16.7, and 17.3±0.2 degrees two-theta; a powder XRD pattern with peaks at about 6.5, 8.6, 14.1, and 16.7±0.2 degrees two-theta; a powder XRD pattern depicted in FIG. 26; a PXRD pattern having at least five peaks selected from the list consisting of: 6.5, 8.6, 14.1, 16.7, 17.3, 22.9, 23.6, 25.4, 26.2±0.2 degrees two-theta; a solid-state $^{13}$C NMR spectrum with signals at about 162.0, 164.0, and 157.5±0.2 ppm; a solid-state $^{13}$C NMR spectrum with signals at about 162.0, 164.0, and 157.5±0.2 ppm; a solid-state $^{13}$C NMR spectrum having chemical shift differences between the signal exhibiting the lowest chemical shift and another in the chemical shift range of 100 to 180 ppm of about 56.7, 54.7, and 50.2±0.1 ppm; a solid-state $^{13}$C NMR spectrum depicted in FIG. 27, and a solid-state $^{13}$C NMR spectrum depicted in FIG. 28.

In one embodiment, the present invention provides crystalline imatinib mesylate characterized by data selected from a group consisting of: a powder XRD pattern having peaks at: 6.5, 8.7, 9.6, 12.7, 14.2 and 16.7±0.2 degrees two-theta; and a powder XRD pattern depicted in FIG. 29.

In another embodiment, the present invention further encompasses a process for preparing the amorphous form of imatinib mesylate by a process comprising: providing a solution of imatinib mesylate in a solvent selected from the group consisting of: methanol, methoxyethanol, ethoxyethanol, N-methylpyrrolidone, propylene carbonate, acetonitrile, nitromethane, pyridine, dimethylsulfoxide, and mixtures thereof; and admixing the solution with an anti-solvent selected from the group consisting of: ethylacetate butylacetate, diethyl ether, tert-butyl methyl ether, tetrahydrofuran, dioxane, methylal, ethylal and 1,3-dioxolane to obtain a precipitate of the amorphous form.

In yet another embodiment, the present invention further encompasses a process for preparing amorphous imatinib mesylate comprising: providing a solution of imatinib mesylate in solvent selected from the group consisting of: isobutanol, n-butanol, methoxyethanol or ethoxyethanol, N-methylpyrrolidone, acetic acid, propylene carbonate, acetonitrile, nitromethane, pyridine, dimethylsulfoxide, and mixture thereof; and cooling the solution to a temperature of about 30° C. to about −50° C. to obtain the amorphous imatinib mesylate.

In one embodiment, the present invention further encompasses a process for preparing crystalline imatinib mesylate Form α by crystallizing Imatinib mesylate from a solution of imatinib mesylate in a solvent selected from the group consisting of: 1,2-propylene carbonate, a mixture of n-propanol, water and acetic acid, and mixtures thereof.

In another embodiment, the present invention encompasses a process for preparing crystalline imatinib mesylate Form α by providing a solution of Imatinib mesylate in ethyleneglycol dimethyl ether, and admixing with tert-butyl dimethylether to form a suspension comprising said crystalline form.

In yet another embodiment, the present invention encompasses a process for preparing crystalline imatinib mesylate Form α by slurrying Imatinib mesylate selected from a group consisting of: forms IX, VIII and mixtures thereof, in a solvent selected from the group consisting of: ethylacetate, acetone, and mixtures thereof.

In one embodiment, the present invention comprises a pharmaceutical composition comprising any one of imatinib mesylate forms of the present invention and at least one pharmaceutically acceptable excipient.

In another embodiment, the present invention comprises a pharmaceutical composition comprising any one of imatinib mesylate forms made by the processes of the present invention, and at least one pharmaceutically acceptable excipient.

In yet another embodiment, the present invention further encompasses a process for preparing a pharmaceutical formulation comprising combining any one of imatinib mesylate forms of the present invention with at least one pharmaceutically acceptable excipient.

In one embodiment, the present invention further encompasses a process for preparing a pharmaceutical formulation comprising combining any one of imatinib mesylate forms made by the processes of the present invention, and at least one pharmaceutically acceptable excipient.

In another embodiment, the present invention further encompasses the use of any one of imatinib mesylate forms of the present invention for the manufacture of a pharmaceutical composition.

In yet another embodiment, the present invention further encompasses the use of any one of imatinib mesylate forms made by the processes of the invention, for the manufacture of a pharmaceutical composition.

BRIEF DESCRIPTION OF THE FIGURES

FIG. 11 illustrates a solid-state $^{13}$C NMR spectrum of imatinib mesylate Form VII in the 100-180 ppm range.

FIG. 12 illustrate a solid-state $^{13}$C NMR spectrum of imatinib mesylate Form VII.

DETAILED DESCRIPTION

Figure 1:
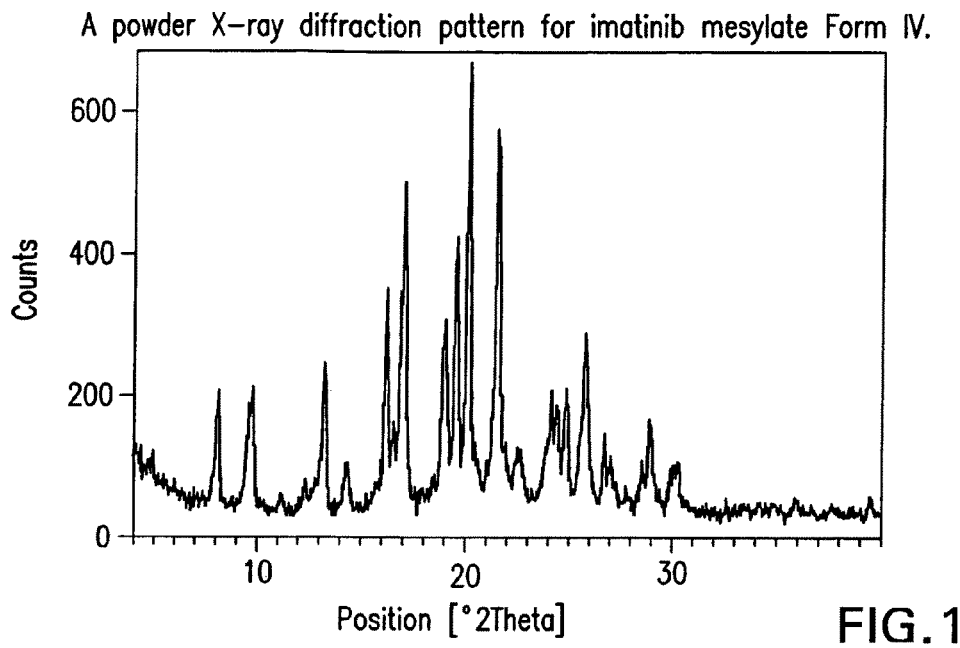
FIG. 1 illustrates a powder X-ray diffraction pattern for imatinib mesylate Form IV.

The present invention presents imatinib mesylate solvates and crystal forms, procedures for preparation thereof and procedures for the preparation of amorphous and α forms. Preferably imatinib mesylate solvate is made up of a solvent selected from the group consisting of: ether, tetrahydrofuran, dioxolane, aliphatic alcohol, nitromethane and acetic acid. The present invention further presents crystalline imatinib mesylate, designated Forms IV, V, VI, VII, VIII, IX, X, XI, XII, XIII, XIV, XV and XVI, methods of preparing crystalline imatinib mesylate, and pharmaceutical compositions comprising crystalline imatinib mesylate.

As used herein, the term "solvate" is meant to include any crystalline form which incorporates a solvent in a level of more than about 1% by weight. The solvent level can be measured by GC when the solvent is other than water, and by KF when the solvent is water.

As used herein, the term room temperature refers to a temperature from about 20° C. to about 30° C.

As used herein, unless otherwise indicated, "imatinib mesylate" includes but is not limited to, all polymorphic forms and amorphous form of imatinib mesylate.

Imatinib base used throughout may be prepared, for example, according to the process disclosed in U.S. Pat. No. 5,521,184, which patent is incorporated herein by reference. In short, imatinib base is prepared by stirring under nitrogen at room temperature a solution of N-(5-amino-2-methylphenyl)-4-(3-pyridyl)-2-pyrimidine-amine and 4-(4-methyl-piperazinomethyl)-benzoyl chloride in 320 ml of pyridine, concentrating the resulting mixture, adding water to this mixture, and cooling the obtained mixture.

As used herein, the term chemical shift difference refers to the difference in chemical shifts between a reference signal and another signal in the same NMR spectrum. In the present patent application the chemical shift differences were calculated by subtracting the chemical shift value of the signal exhibiting the lowest chemical shift (reference signal) in the solid state $^{13}$C NMR spectrum in the range of 100 to 180 ppm from chemical shift value of another (observed) signal in the same $^{13}$CNMR spectrum in the range of 100 to 180 ppm. These chemical shift differences are to provide a measurement for a substance, for example Imatinib mesylate of the present invention, compensating for a phenomenon in NMR spectroscopy wherein, depending on the instrumentation, temperature, and calibration method used, a shift in the solid-state NMR "fingerprint" is observed. This shift in the solid-state NMR "fingerprint", having chemical shift resonances at a certain positions, is such that although the individual chemical shifts of signals have altered, the difference between chemical shifts of each signal and another is retained.

As used herein, the abbreviation PXRD refers to powder X-ray diffraction and the term NMR refers to nuclear magnetic resonance.

As used herein, the term room temperature refers to a temperature of about 20° C. to about 25° C.

The present invention provides imatinib mesylate solvates.

The present invention provides imatinib mesylate solvates with solvents selected from the group consisting of: aliphatic alcohols, ethers, dioxolane, nitromethane and acetic acid. Preferably, the aliphatic alcohol is a $C_{2-4}$ aliphatic alcohol, more preferably the $C_{2-4}$ aliphatic alcohol is ethanol or isopropanol. Preferably, the ether is a $C_{3-5}$ ether, more preferably a $C_{3-5}$ cyclic ether, most preferably tetrahydrofuran. Preferably, dioxolane is 1,3-dioxolane.

Figure 2:
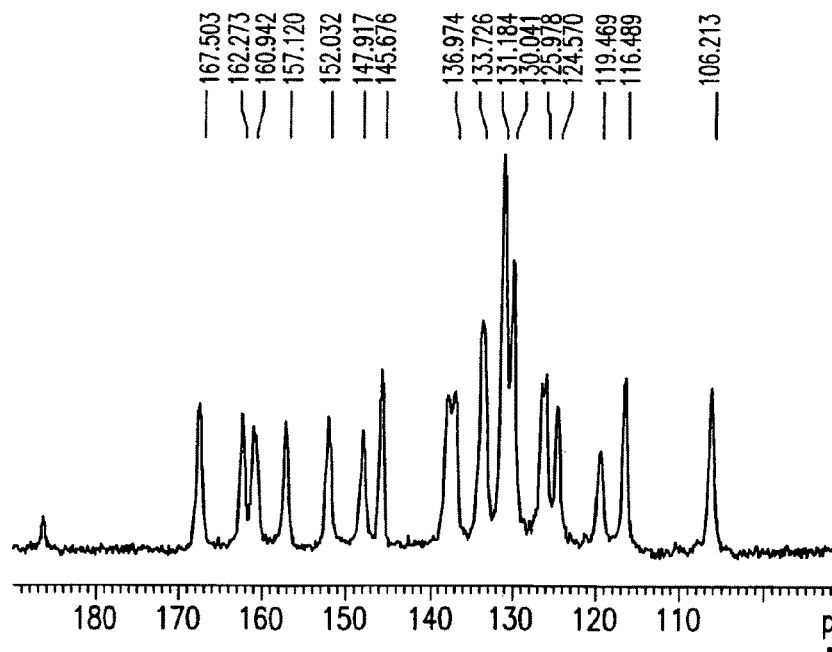
FIG. 2 illustrates a solid-state $^{13}$C NMR spectrum of imatinib mesylate Form IV in the 100-180 ppm range.
Figure 3:
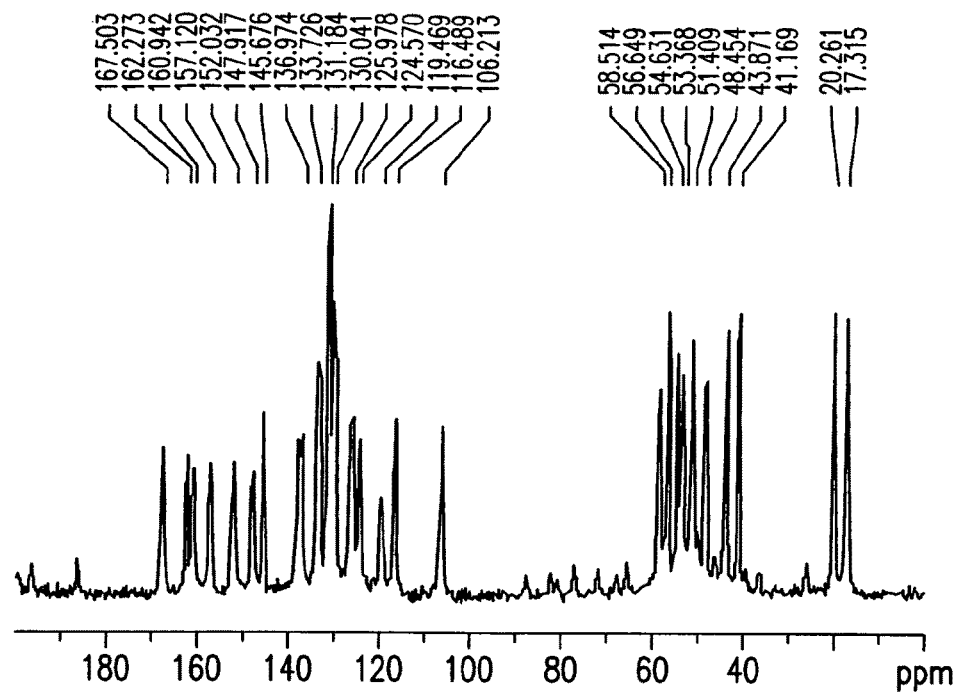
FIG. 3 illustrates a solid-state $^{13}$C NMR spectrum of imatinib mesylate Form IV.

The present invention provides crystalline imatinib mesylate, designated Form IV, characterized by data selected from the group consisting of: a powder XRD pattern with peaks at about 8.1, 9.7, 17.0, 20.1, and 21.5±0.2 degrees two-theta; a powder XRD pattern with peaks at about 8.1, 9.7, 13.2, 16.2, and 17.0±0.2 degrees two-theta; a powder XRD pattern having peaks at about 8.1, 9.7, 16.2, 17.0 and 21.5±0.2 degrees two-theta; a PXRD pattern having at least five peaks selected from the list consisting of peaks at about 8.1, 9.7, 13.2, 14.3, 16.2, 17.0, 24.1, 24.8, 25.8, 26.6, 28.9, 30.3±0.2 degrees two-theta; a powder XRD pattern depicted in FIG. 1; a solid-state $^{13}$C NMR spectrum with signals at about 162.3, 160.9, 157.1±0.2 ppm; a solid-state $^{13}$C NMR spectrum having chemical shifts differences between the signal exhibiting the lowest chemical shift and another in the chemical shift range of 100 to 180 ppm of about 56.1, 54.7 and 50.9±0.1 ppm, a $^{13}$C NMR spectrum depicted in FIG. 2, and a and a solid-state $^{13}$C NMR spectrum depicted in FIG. 3. The signal exhibiting the lowest chemical shift in the chemical shift area of 100 to 180 ppm is typically at about 106.2±1 ppm.

The above crystalline imatinib mesylate may be further characterized by data selected from the group consisting of: a powder XRD pattern with peaks at about 9.5, 13.2, 14.3, 16.2, 24.1, 24.8 and 25.8±0.2 degrees two-theta; a solid-state $^{13}$C NMR spectrum having signals at about 152.0, 147.9 and 145.7±0.2 ppm; and a solid-state $^{13}$C NMR spectrum having chemical shift differences between the signal exhibiting the lowest chemical shift and another in the chemical shift range of 100 to 180 ppm in the chemical shift range of 100 to 180 ppm of about 45.8, 41.7 and 39.5±0.1 ppm.

In addition the above crystalline imatinib mesylate may be further characterized by data selected from the group consisting of: a solid-state $^{13}$C NMR spectrum having signals at about 20.3 and 17.3±0.2 ppm; and a solid-state $^{13}$C NMR spectrum having chemical shift differences between the two signals exhibiting the lowest two chemical shifts in the chemical shift range of less than 100±0.1 ppm of about 3.0±0.1 ppm. The signal exhibiting the lowest chemical shift in the chemical shift range of 100 to 180 ppm is, typically, at about 106.2±1 ppm.

The above crystalline imatinib mesylate is an ethanol solvate of Imatinib mesylate. Preferably, the crystalline form contains about 5% to about 9%, more preferably about 7% to about 8% by weight of ethanol as measured by GC. Furthermore, the presence of ethanol in the structure of the solvate can also be characterized by the presence of sharp signals at about 20.3 ppm (methyl) and at 56.6 ppm (methylene) in the solid-state $^{13}$C NMR spectrum.

The said crystalline imatinib mesylate can be used as an intermediate for the preparation of other forms of imatinib mesylate, such as, form XIII that is described bellow. Also, the prior art discloses mostly anhydrous forms of Imatinib mesylate, while the said crystalline imatinib mesylate is an ethanol solvate that is characterized by small particle size of less than 100 microns, hence, the dissolution rate is expected to be very fast and therefore it should have a better bioavailability. Accordingly, the above crystalline imatinib mesylate extends the formulation possibilities.

The present invention further encompasses a process for preparing the imatinib mesylate Form IV comprising: providing a solution of imatinib mesylate and ethanol; and cooling the solution to a temperature of about 10° C. to about −50° C. to obtain a precipitate of the said crystalline form; and recovering the said crystalline form.

The imatinib mesylate solution may be prepared from imatinib mesylate by suspending imatinib mesylate in ethanol and heating the suspension to a temperature of about 25° C. to about reflux, preferably to about 50° C. to about 78° C., more preferably to about 50° C. to 60° C., to obtain a solution. A suitable concentration of imatinib mesylate in ethanol preferably can range from about 1:5 to about 1:30 in weight (g) imatinib mesylate to volume (ml) ethanol.

Alternatively, the imatinib mesylate solution may be prepared by combining imatinib base, ethanol and methanesulfonic acid. Preferably, this process comprises: suspending imatinib base in ethanol at a temperature below 0° C.; admixing methanesulfonic acid in stoichiometric amount; and maintaining the mixture at below 0° C., preferably to obtain a solution of imatinib mesylate. Preferably, the imatinib base is suspended in ethanol at a temperature of about 0° C. to about −40° C., more preferably, at about −5° C. to about −20° C., most preferably at about −10° C. Preferably, the said mixture is maintained at a temperature of about 0° C. to about −20° C., preferably at about 0° C. to about −10° C., more preferably at about −5° C. Preferably, maintaining is by continuous stirring. It is worthy to note that in this case, the solution may be short lived and crystallization occurs shortly thereafter.

Preferably, precipitating the said crystalline form of imatinib mesylate is performed by cooling to a temperature of about 0° C. to about −40° C., more preferably, to a temperature of about 0° C. to about −20° C., more preferably to a temperature of about −5° C. to about −20° C., most preferably to a temperature of about −5° C. to about −15° C. Preferably, precipitating is without stirring. Preferably, during precipitation, a solvent in which is imatinib mesylate is insoluble, for example, tert-butylmethyl ether, can be added in order improve the yield of crystallization. Recovery of the crystalline imatinib mesylate Form IV, if desired, may be performed by any means known in the art such as by filtering, washing and drying. Preferably, washing is with petrolether or t-butyl methyl ether.

Figure 4:
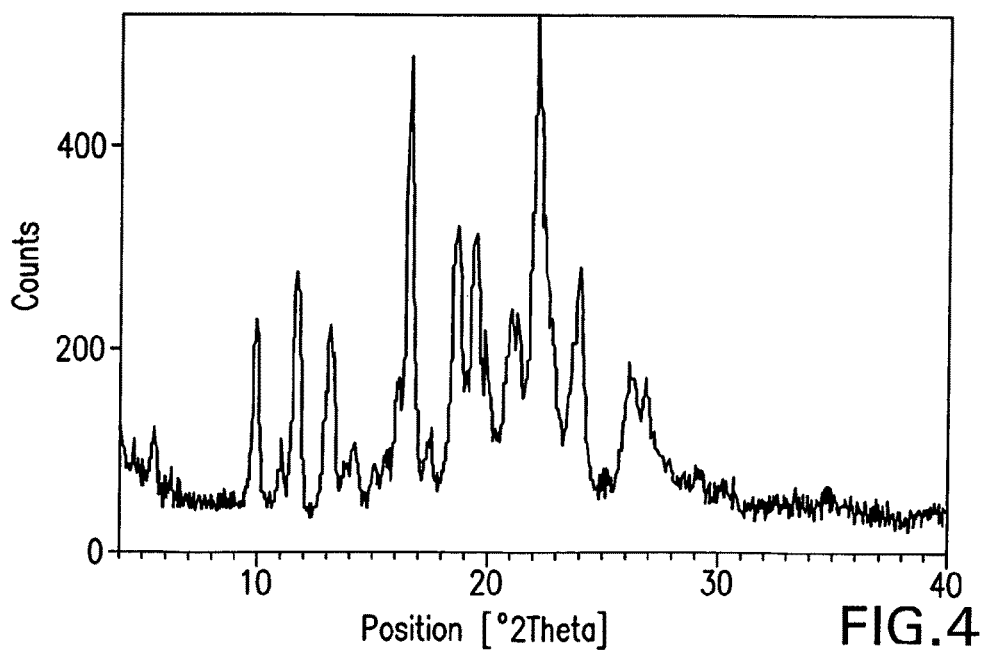
FIG. 4 illustrates a powder X-ray diffraction pattern for imatinib mesylate Form V.
Figure 5:
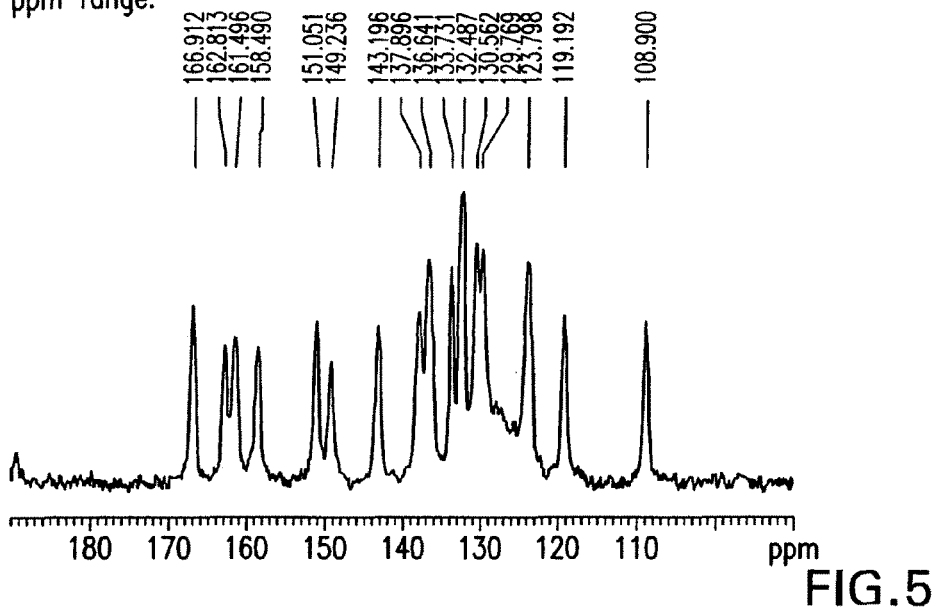
FIG. 5 illustrates a solid-state $^{13}$C NMR spectrum of imatinib mesylate Form V in the 100-180 ppm range.
Figure 6:
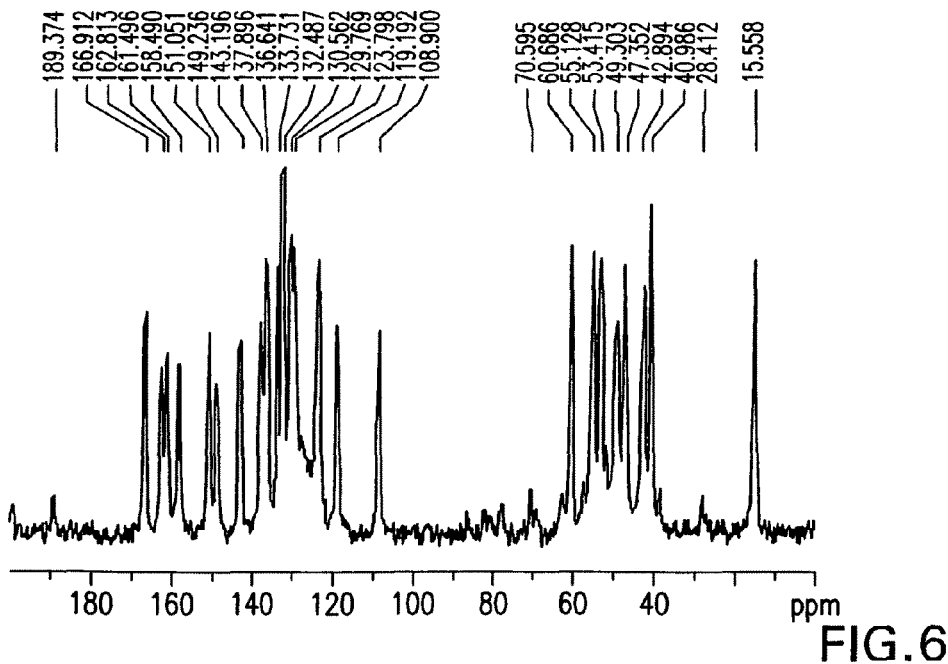
FIG. 6 illustrates a solid-state $^{13}$C NMR spectrum of imatinib mesylate Form V.

The present invention also provides crystalline imatinib mesylate, designated Form V, characterized by data selected from the group consisting of: a powder XRD pattern with peaks at about 9.9, 11.7, 13.3, 16.6, and 22.1±0.2 degrees two-theta; a powder XRD pattern with peaks at about 9.9, 11.7, 13.3, and 16.6±0.2 degrees two-theta; a PXRD pattern having peaks at about: 5.6, 9.9, 11.7, 13.3, 16.6, and 18.5±0.2 degrees two-theta; a PXRD pattern having at least five peaks selected from the list consisting of peaks at about: 5.6, 9.9, 11.7, 13.3, 16.6, 18.5, 22.1, 24.0, 26.2, 26.9±0.2 degrees two-theta; a PXRD pattern depicted in the FIG. 4; a solid-state $^{13}$C NMR spectrum with signals at about 162.8, 161.5, 158.5±0.2 ppm; a solid-state $^{13}$C NMR spectrum having chemical shifts differences between the signal exhibiting the lowest chemical shift and another in the chemical shift range of 100 to 180 ppm of about 53.9, 52.6 and 49.6±0.1 ppm, a solid state $^{13}$C NMR depicted in FIG. 5, and a solid state $^{13}$C NMR spectrum depicted in FIG. 6. The signal exhibiting the lowest chemical shift in the chemical shift range of 100 to 180 ppm is typically at about 108.9±1 ppm.

In addition, this crystalline imatinib mesylate may be further characterized by data selected from the group consisting of: a powder XRD pattern with peaks at about 18.5, 19.5, 20.9, and 24.0±0.2 degrees two-theta; a powder XRD pattern having peaks at about: 19.5, 22.1, and 24.0±0.2 degrees two-theta; a solid-state $^{13}$C NMR spectrum with signals at about 151.1 and 149.2±0.2 ppm; and a solid-state $^{13}$C NMR spectrum having chemical shift differences between the signal exhibiting the lowest chemical shift and another in the chemical range of 100 to 180 ppm of about 42.2 and 40.3±0.1 ppm.

Also, this crystalline imatinib mesylate can be further characterized by a solid-state $^{13}$C NMR spectrum having signals at about 15.6±0.2 ppm.

Furthermore, this crystalline imatinib mesylate may contain a residual amount 1,3-dioxolane as measured by GC. Preferably, the residual amount is less than about 1000 ppm, more preferably, up to about 200 ppm, as measured by GC. Also, the crystalline form contains up to 3%, preferably, up to 1% of water by weight as measured by KF.

Figure 32:
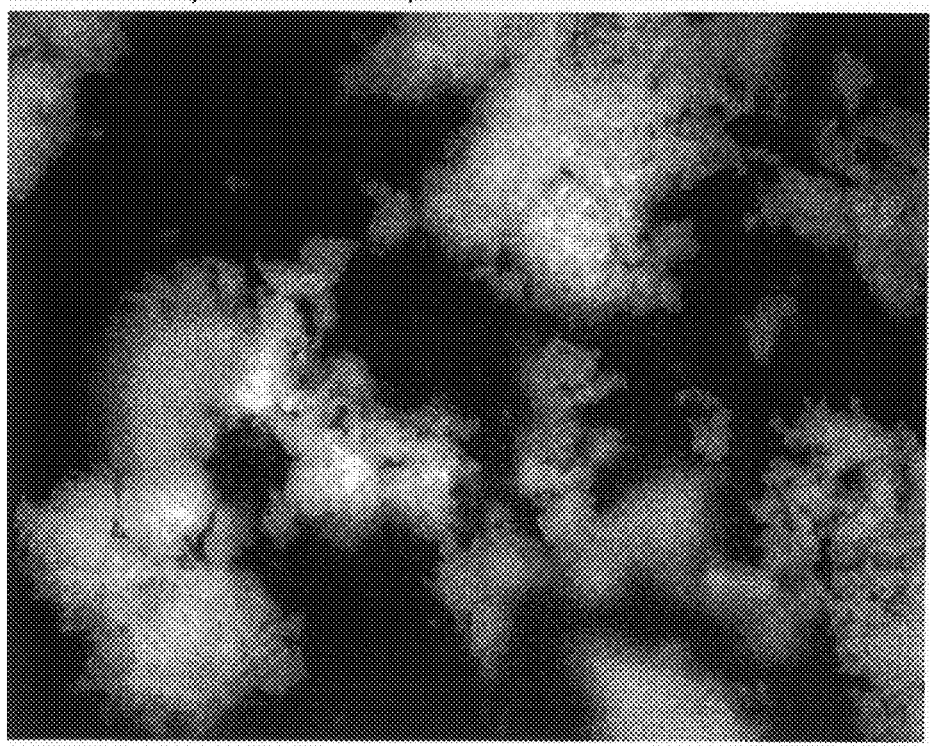
FIG. 32 illustrates an optical microscope photo of imatinib mesylate form V from an optical microscope in fluorescence mode.

The said crystalline imatinib mesylate can be prepared by heating other forms of imatinib mesylate, such as, form VI that is described bellow. Also, the said form is characterized by a small particle size, as depicted in FIG. 32, hence, the dissolution rate is expected to be very fast and therefore it should have a better bioavailability. Furthermore, the above form is found to be stable under pressure as well as under heating up to a temperature of 80° C. Hence, this form is attractive for formulations.

Crystalline form V is prepared by a process comprising drying crystalline Form VI at a temperature of about room temperature to about 90° C. Preferably, the drying temperature is about 40° C. to about 90° C., more preferably, of about 55° C. to about 70° C., most preferably about 60° C. The drying process is carried out for a period of about 12 hours to about 24 hours, preferably for about 18 hours.

Figure 7:
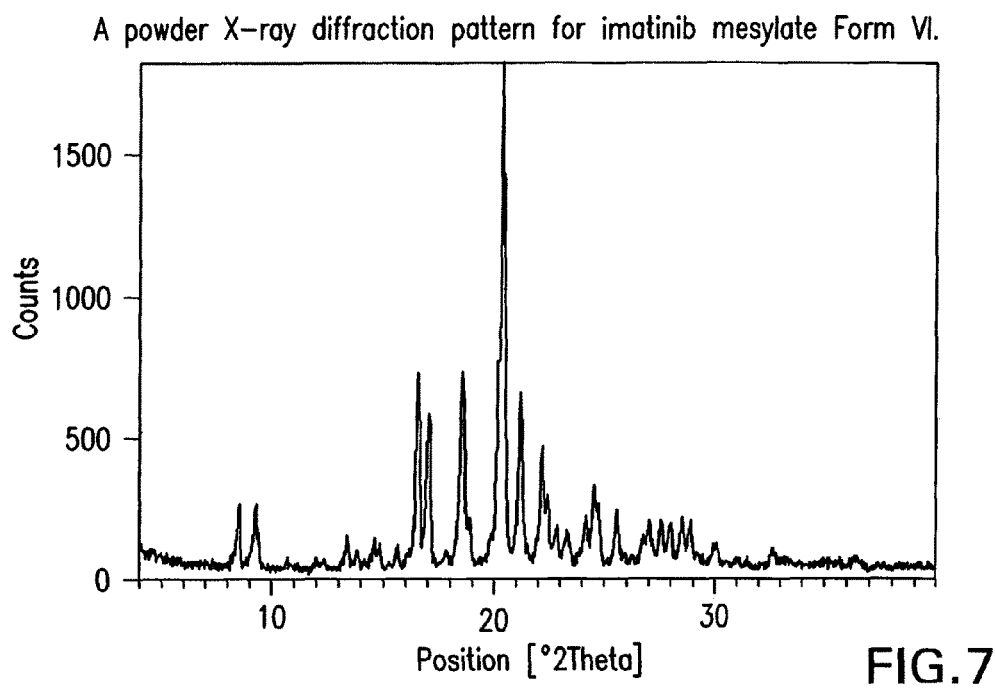
FIG. 7 illustrates a powder X-ray diffraction pattern for imatinib mesylate Form VI.
Figure 8:
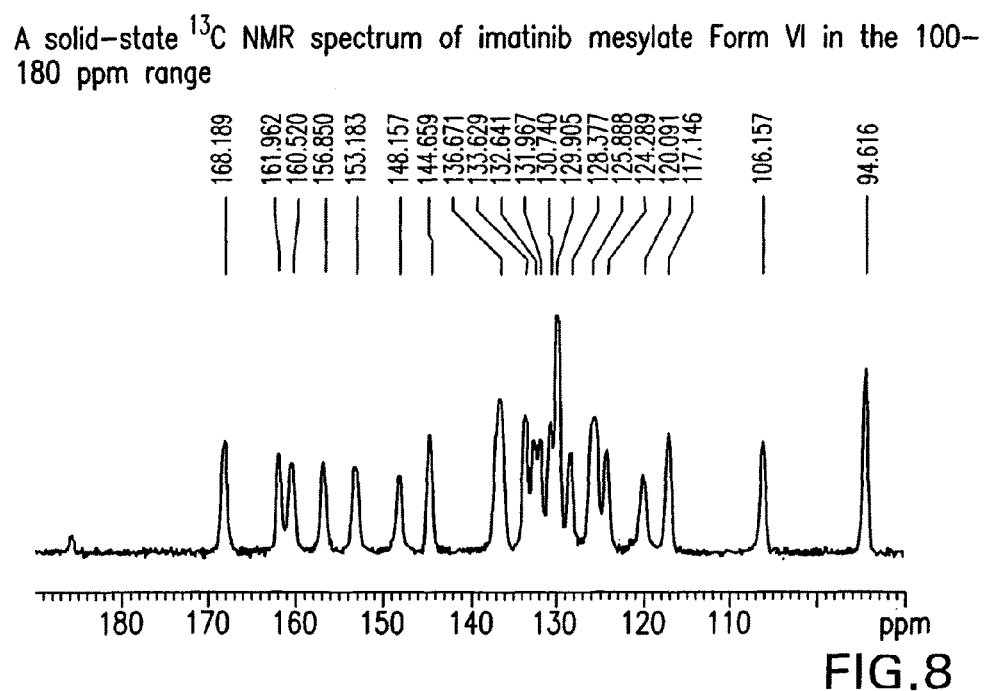
FIG. 8 illustrates a solid-state $^{13}$C NMR spectrum of imatinib mesylate Form VI in the 100-180 ppm range.
Figure 9:
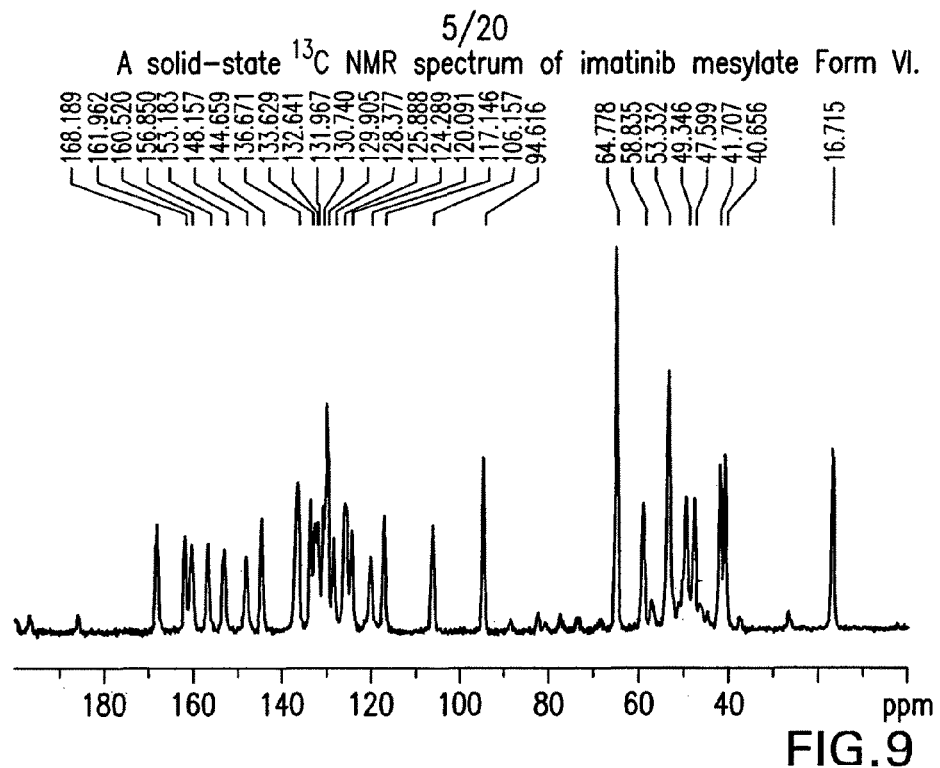
FIG. 9 illustrates a solid-state $^{13}$C NMR spectrum of imatinib mesylate Form VI.

The present invention provides crystalline imatinib mesylate, designated Form VI, characterized by data selected from the group consisting of: a powder XRD pattern with peaks at about 16.6, 17.1, 18.6, 20.4, and 21.2±0.2 degrees two-theta; a powder XRD pattern with peaks at about 8.5, 9.2, 16.6, and 17.1±0.2 degrees two-theta; a powder XRD pattern having peaks at about 8.5, 16.6, 17.1, and 18.6±0.2 degrees two-theta; a powder XRD pattern having at least five peaks selected from the list consisting of peaks at about: 8.5, 9.2, 16.6, 17.1, 18.6, 22.2, 24.6, 25.4±0.2 degrees two-theta; a PXRD pattern depicted in FIG. 7; a solid-state $^{13}$C NMR spectrum having signals at about 162.0, 160.5 and 156.9, 153.2±0.2 ppm; a solid-state $^{13}$C NMR spectrum having chemical shift differences between the signal exhibiting the lowest chemical shift and another in the chemical shift range of 100 to 180 ppm of about 55.8, 54.4, 50.7 and 47.0±0.1 ppm; a solid state $^{13}$C NMR spectrum depicted in FIG. 8, and a solid-state $^{13}$C NMR spectrum depicted in FIG. 9. The signal exhibiting the lowest chemical shift in the chemical shift range of 100 to 180 ppm is, typically, at about 106.2±1 ppm.

In addition, this crystalline imatinib mesylate may be further characterized by data selected from the group consisting of: a powder XRD pattern with peaks at about 8.5, 9.2, 22.2, and 24.5±0.2 degrees two-theta; a powder XRD pattern with peak at about: 20.4, 21.2, 22.2, and 24.5±0.2 degrees two-theta; a solid-state $^{13}$C NMR spectrum having signals at about 148.2 and 144.7±0.2 ppm; and a solid-state $^{13}$C NMR spectrum having chemical shift differences between the signal exhibiting the lowest chemical shift and another in the chemical shift range of 100 to 180 ppm of about 42.0 and 38.5±0.1 ppm.

Also, this crystalline imatinib mesylate may be further characterized by a solid-state $^{13}$C NMR spectrum having signals at about 16.7±0.2 ppm.

The above crystalline imatinib mesylate is a 1,3-dioxalane solvate of imatinib mesylate. Preferably, the crystalline form contains about 6% to about 13%, more preferably about 7% to about 8% by weight of 1,3-dioxalane as measured by GC. Furthermore, the presence of 1,3-dioxalane in the structure of the solvate can also be characterized by the presence of sharp signals at 64.8 ppm (methylene) and at 94.6 ppm (methylene) in the solid-state $^{13}$CNMR spectrum. The content of 1,3-dioxolane in Form VI can be decreased down to 6% by weight as measured by GC by gentle heating.

The said crystalline imatinib mesylate can be an intermediate for other forms of Imatinib mesylate, such as form V. Also, the said form is characterized by a small particle size, of less than 100 microns, hence, the dissolution rate is expected to be very fast and therefore it should have a better bioavailability. Hence, this form is attractive for formulations.

The present invention further encompasses a process for preparing crystalline imatinib mesylate form VI comprising: crystallizing imatinib mesylate from a solution of imatinib mesylate in aqueous 1,3-dioxolane to obtain a precipitate; and recovering the crystalline imatinib mesylate.

The imatinib mesylate solution can be prepared from imatinib base or imatinib mesylate. In one example, the process comprises: preparing a suspension of imatinib base in 1,3-dioxolane and admixing methanesulfonic acid. Preferably, the suspension of imatinib base is prepared by suspending imatinib base in aqueous 1,3-dioxolane at temperature of about 110° C. to about 78° C., preferably about 10° C. to about 30° C., more preferably about 10° C. to about 20° C. Addition of methanesulfonic acid facilitates the dissolution of imatinib base. Preferably, the methanesulfonic acid is dissolved in 1,3-dioxolane. Preferably, a stoichiometric amount of methanesulfonic acid is added. Preferably, crystallizing is by cooling the solution.

Preferably, cooling is at a temperature of about −20° C. to about 20° C., more preferably from about −10° C. to about 10° C., most preferably about 0° C. to about 10° C. The solution is cooled for a period of time to obtain crystalline imatinib mesylate, preferably the period is from about 1 hour to about 24 hours, more preferably from about 4 hours to about 16 hours, most preferably for about 4 to about 8 hours.

Alternatively, the solution can be prepared by dissolving imatinib mesylate in aqueous 1,3-dioxolane at a temperature of about 10° C. to about 78° C., more preferably about 50° C. to about 78° C., even more preferably from about 60° C. to about 75° C., most preferably, to about 71° C. A suitable concentration of imatinib mesylate in 1,3-dioxolane preferably can range from about 1:5 to about 1:30 in weight (g) imatinib mesylate to volume (ml) ethanol.

The obtained imatinib mesylate Form VI may then be recovered by any means known in the art such as by filtering, and washing. Preferably, the recovery doesn't include a drying step, since this may result in a conversion of form VI to form V. Preferably, the washing is with 1,3-dioxolane. As one skilled in the art will appreciate, the time required to obtain Form VI will vary depending upon, among other factors, the amount of precipitate to be heated and the heating temperature, and can be determined by taking periodic XRD readings.

Figure 10:
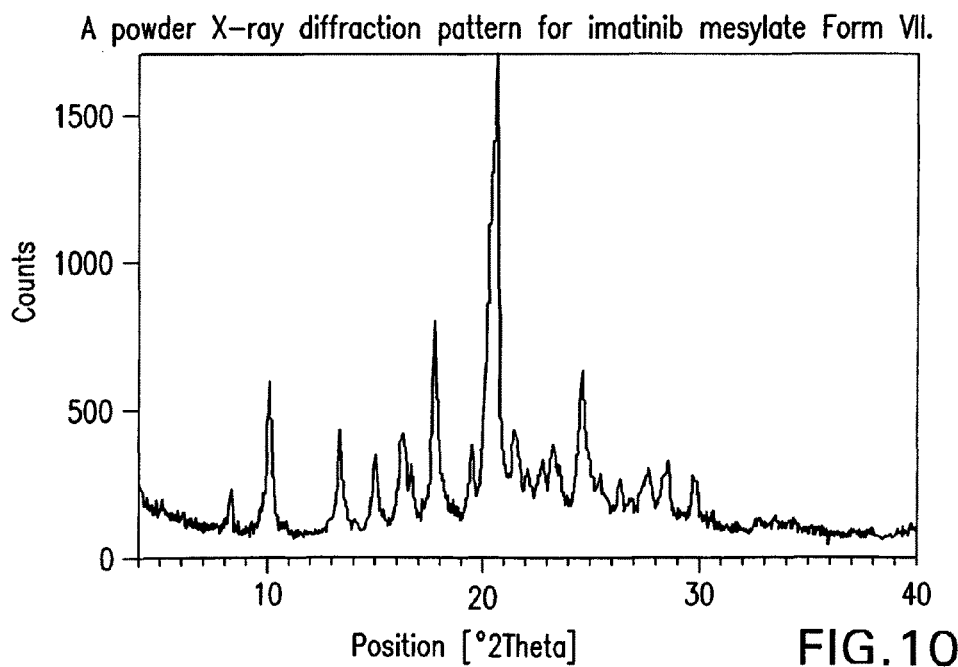
FIG. 10 illustrates a powder X-ray diffraction pattern for imatinib mesylate Form VII.

The present invention provides crystalline imatinib mesylate, designated Form VII, characterized by data selected from the group consisting of: a powder XRD pattern with peaks at about 10.1, 13.4, 17.7, 20.6, and 24.6±0.2 degrees two-theta; a powder XRD pattern with peaks at about 10.1, 13.4, 15.0, 16.2, and 17.7±0.2 degrees two-theta; a powder XRD pattern having at least five peaks selected from a list consisting of peaks at about: 8.2, 10.1, 13.4, 15.0, 16.2, 17.7, 19.4, 24.6, 28.5, 29.7±0.2 degrees two-theta; a PXRD pattern depicted in the PXRD pattern in FIG. 10; a solid-state $^{13}$C NMR spectrum having signals at about 159.0, 150.9 and 146.5±0.2 ppm; a solid-state $^{13}$C NMR spectrum having chemical shift differences between the signal exhibiting the lowest chemical shift and another in the chemical shift range of 100 to 180 ppm of about 54.1, 46.0 and 41.6±0.1 ppm; a solid state $^{13}$C NMR spectrum depicted in FIG. 11, and a and a solid-state $^{13}$C NMR spectrum depicted in FIG. 12. The signal exhibiting the lowest chemical shift in the chemical shift range of 100 to 180 ppm is, typically, at about 104.9±1 ppm.

In addition, this crystalline imatinib mesylate may be further characterized by data selected from the group consisting of: a powder XRD pattern with peaks at about 15.0, 16.2, 19.4 and 21.4±0.2 degrees two-theta; a powder XRD pattern with peaks at about: 20.6, and 24.6±0.2 degrees two-theta; a solid-state $^{13}$C NMR spectrum having signals at about 141.6 and 139.0±0.2 ppm; and a solid-state $^{13}$C NMR spectrum having chemical shift differences between the signal exhibiting the lowest chemical shift and another in the chemical shift range of 100 to 180 ppm of about 36.7 and 34.1±0.1 ppm.

Also, this crystalline imatinib mesylate may be further characterized by a solid-state $^{13}$C NMR spectrum having a signals at about 18.7±0.2 ppm.

The above crystalline imatinib mesylate is a nitromethane solvate of imatinib mesylate. Preferably, the crystalline form contains about 7% to about 12%, more preferably about 7% by weight of nitromethane as measured by GC.

The said crystalline imatinib mesylate can be an intermediate for other forms of Imatinib mesylate, such as form β. Also, the said form is characterized by a small particle size, of less than 100 microns, hence, the dissolution rate is expected to be very fast and therefore it should have a better bioavailability. Hence, this form is attractive for formulations.

The present invention further encompasses a process for preparing imatinib mesylate form VII by a process comprising: providing a solution of imatinib mesylate in nitromethane; and cooling the solution to obtain crystalline imatinib mesylate Form VII.

The imatinib mesylate solution may be prepared from imatinib mesylate or imatinib base. This process comprises: providing a solution of imatinib base and nitro methane and admixing methanesulfonic acid. Preferably, the solution of imatinib base is prepared by dissolving imatinib base in nitromethane at a temperature of about 60° C. to about 100° C., more preferably about 70° C. to about 90° C., most preferably about 90° C. Preferably, a stoichiometric amount of methanesulfonic acid is added.

Preferably, the cooling is to a temperature of about 20° C. to about 0° C., more preferably to about 10° C. to about 0° C., most preferably to about 10° C. Preferably, the cooling is done for a period of time to obtain crystalline imatinib mesylate form VII. As one skilled in the art will appreciate, the time required to obtain crystalline imatinib mesylate will vary depending upon, among other factors, the amount of precipitate to be heated and the heating temperature, and can be determined by observing the process. Preferably, the period of time to obtain crystalline imatinib mesylate form VII when cooling a solution of imatinib mesylate in nitromethane is from about 3 hours to about 10 hours, more preferably from about 5 hours to about 10 hours, most preferably about 5 hours. The obtained imatinib mesylate Form VII may then be recovered by any means known in the art such as by filtering, washing and drying. Preferably, the washing is with t-butyl methyl ether. Preferably, the drying is with nitrogen, more preferably, under vacuum.

Figure 13:
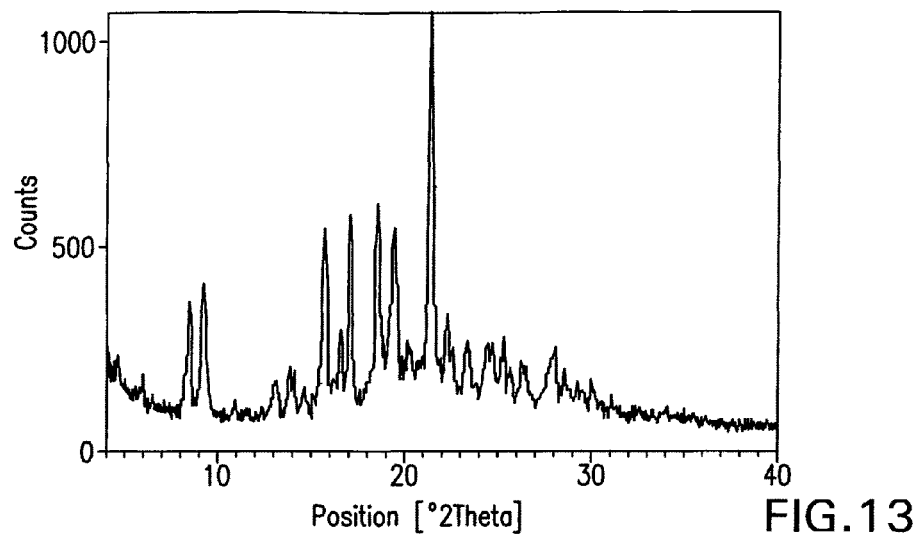
FIG. 13 illustrates a powder X-ray diffraction pattern for imatinib mesylate Form VIII.
Figure 14:
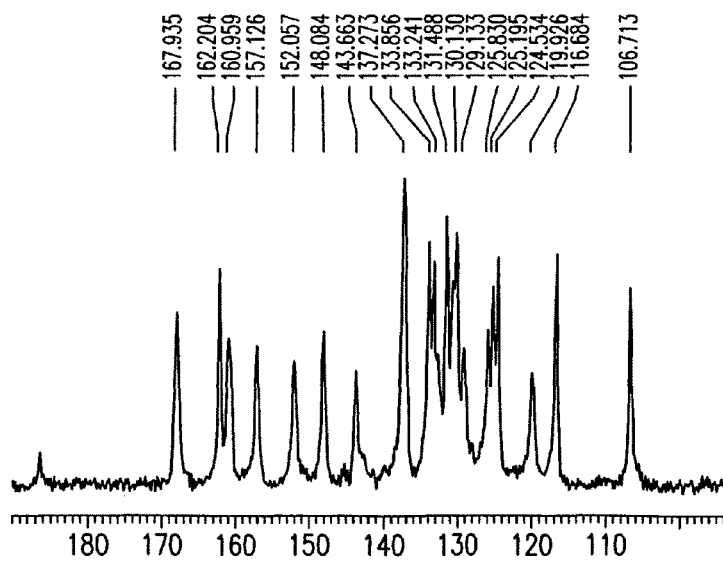
FIG. 14 illustrates a solid-state $^{13}$C NMR spectrum of imatinib mesylate Form VIII in the 100-180 ppm range.
Figure 15:
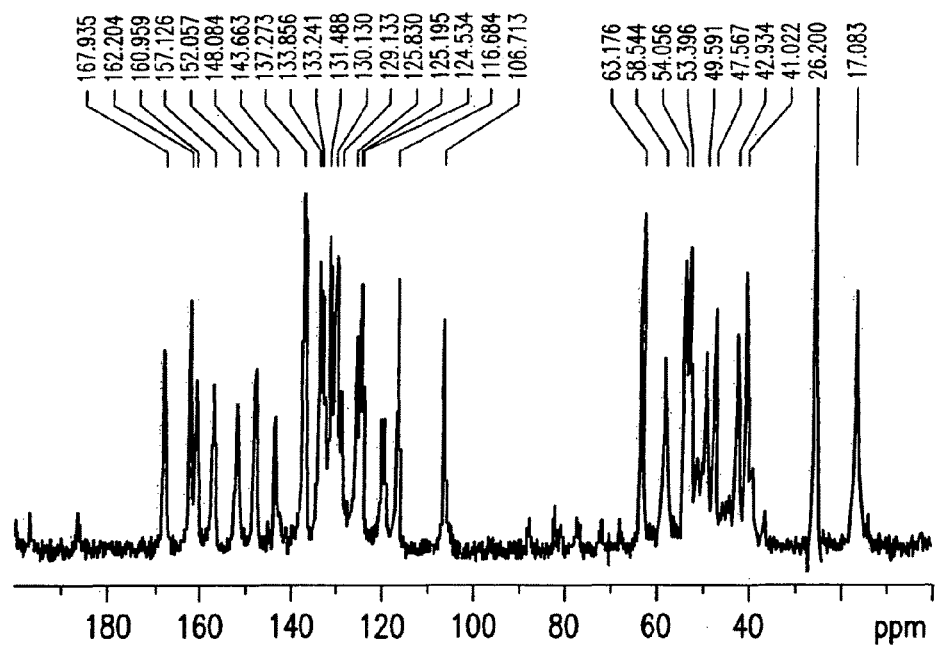
FIG. 15 illustrates a solid-state $^{13}$C NMR spectrum of imatinib mesylate Form VIII.

The present invention provides crystalline imatinib mesylate, designated Form VIII, characterized by data selected from the group consisting of: a powder XRD pattern with peaks at about 8.5, 9.3, 15.8, 17.1, and 21.4±0.2 degrees two-theta; a powder XRD pattern with peaks at about 8.5, 9.3, 15.8, and 17.1±0.2 degrees two-theta; a powder XRD pattern having peaks at about: 8.5, 9.3, 15.8, 17.1 and 18.5±0.2 degrees two-theta; a powder XRD pattern having at least five peaks selected from the list consisting of peaks at about: 8.5, 9.3, 13.2, 13.8, 14.6, 15.8, 16.6, 17.1, 18.5, 19.4, 21.4, 22.3±0.2 degrees two-theta; a powder XRD pattern depicted in FIG. 13; a solid-state $^{13}$C NMR spectrum having signals at about 162.2, 161.0, 157.1±0.2 ppm; a solid-state $^{13}$C NMR spectrum having chemical shift differences between the signal exhibiting the lowest chemical shift and another in the chemical shift range of 100 to 180 ppm of about 55.5, 54.3 and 50.4±0.1 ppm; a solid-state $^{13}$C NMR spectrum depicted in FIG. 14, and a solid-state $^{13}$C NMR spectrum depicted in FIG. 15. The signal exhibiting the lowest chemical shift in the chemical shift range of 100 to 180 ppm is, typically, at about 106.7±1 ppm.

In addition, this crystalline imatinib mesylate may be further characterized by data selected from the group consisting of: a powder XRD pattern having peaks at about 16.6, 18.5, 19.4, and 22.3±0.2 degrees two-theta, a powder XRD pattern having peaks at about: 19.4, and 21.4±0.2 degrees two-theta; a solid-state $^{13}$C NMR spectrum having signals at about 152.1, 148.1 and 143.7±0.2 ppm; and a solid-state $^{13}$C NMR spectrum having chemical shift differences between the signal exhibiting the lowest chemical shift and another in the chemical shift range of 100 to 180 ppm of about 45.3, 41.4 and 37.0±0.1 ppm.

Also, this crystalline imatinib mesylate can be further characterized by a solid-state $^{13}$C NMR spectrum having signals at about 17.1 and 26.2±0.2 ppm.

The above crystalline imatinib mesylate is an isoproapnol solvate of imatinib mesylate. Preferably, the crystalline form contains about 7% to about 11%, more preferably about 7% to about 8% by weight of isopropanol as measured by GC. The crystalline form also contains less than 1% by weight of water, as measured by KF. Furthermore, the presence of isopropanol in the structure of the solvate can also be characterized by the presence of sharp signals at 26.2 ppm (methyl) and at 58.5 ppm (methine) in the solid-state $^{13}$CNMR spectrum.

The said crystalline imatinib mesylate can be an intermediate for other forms of Imatinib mesylate, such as amorphous form. The transformation can be done by heating. Also, the said crystalline imatinib mesylate is characterized by a small particle size, of less than 100 microns, hence, the dissolution rate is expected to be very fast and therefore it should have a better bioavailability. Hence, this form is attractive for formulations.

The present invention further encompasses a process for preparing imatinib mesylate form VIII comprising: providing a solution of imatinib mesylate in isopropanol containing up to 7% by weight of water; and precipitating by cooling to a temperature of about −20° C. to about 20° C. to obtain a precipitate of imatinib mesylate form VIII.

The solution of imatinib mesylate and isopropanol is prepared by a process comprising: providing a suspension of imatinib base and isopropanol containing up to 7% by weight of water; admixing the suspension with cooled methanesulfonic acid; and maintaining the mixture at the cooled temperature to obtain a solution of imatinib mesylate. Preferably, the suspension of imatinib base is prepared by suspending imatinib base in isopropanol containing up to 7% by weight of water at a temperature of about −10° C. to about −5° C., more preferably, at a temperature of about −10° C. Preferably, the isopropanol contains up to 5% of water by weight. Preferably, methanesulfonic acid is added to the suspension at a temperature of about 0° C. to about −10° C., more preferably at a temperature of about −10° C., most preferably in a stoichiometric amount. Preferably, the solution is maintained at a temperature of about 0° C. to about −20° C., more preferably, at a temperature of about −15° C. Preferably, the solution is maintained for a period of about 10 hours to about 24 hours, more preferably for about 12 hours to about 16 hours, most preferably about 12 hours.

Alternatively, the solution of imatinib mesylate and isopropanol can be prepared by a process comprising: suspending imatinib mesylate in isopropanol and heating the suspension to a temperature of about 30° C. to about 83° C. to obtain a solution. Preferably, the suspension is heated to a temperature of about 50° C. to about 83° C., more preferably to about 60° C. to about 80° C. Preferably, the isopropanol contains 95% of isopropanol and 5% of water by weight. A suitable concentration of imatinib mesylate in isopropanol preferably can range from about 1:5 to about 1:30 in weight (g) imatinib mesylate to volume (ml) ethanol.

Preferably, the cooling is to a temperature to about 0° C. to about −20° C., more preferably to a temperature of about −10° C. to about 15° C., most preferably to a temperature of about −5° C. to about 15° C.

Figure 16:
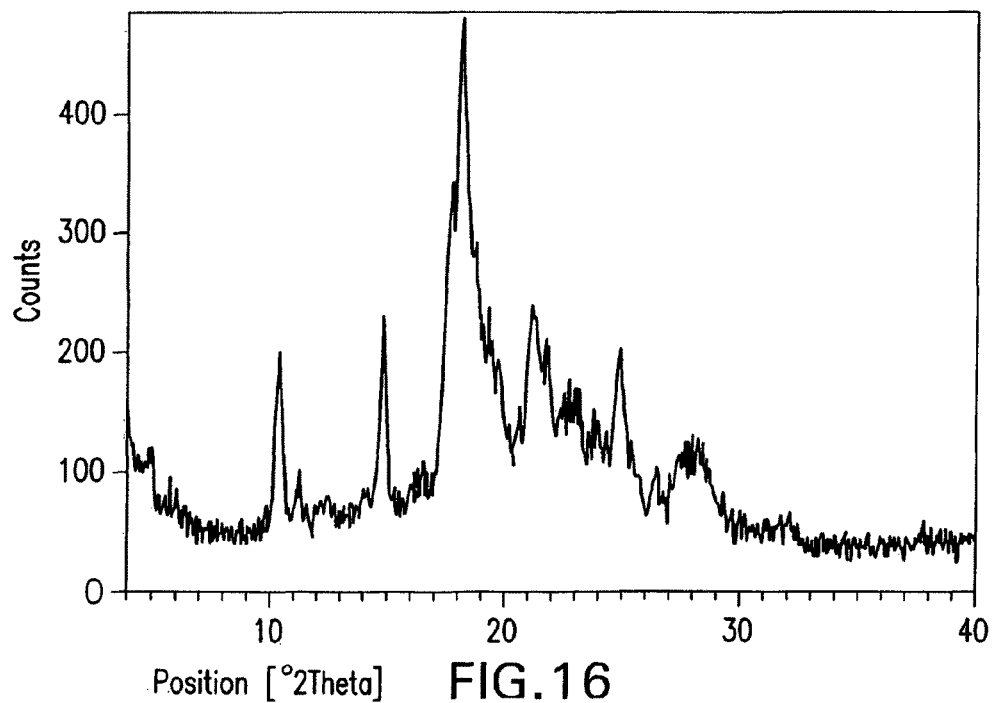
FIG. 16 illustrates a powder X-ray diffraction pattern for imatinib mesylate Form IX.
Figure 17:
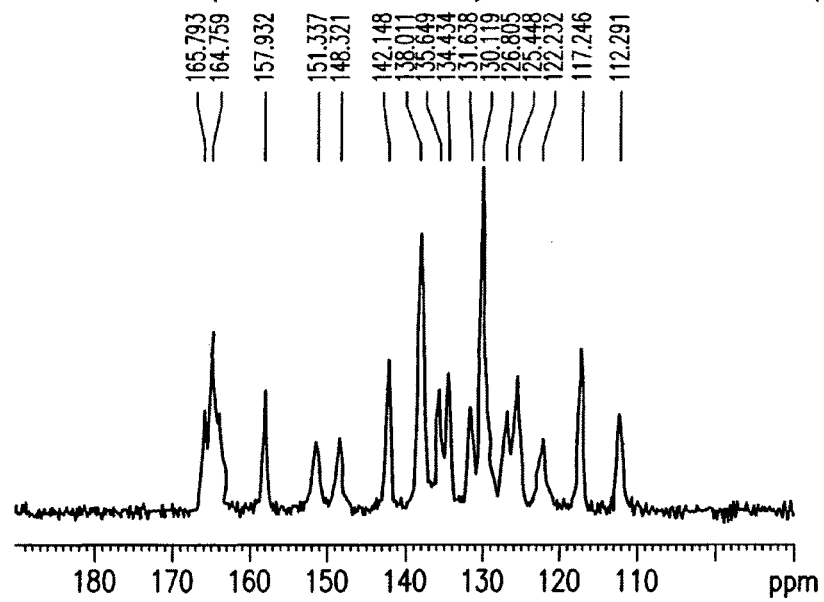
FIG. 17 illustrates a solid-state $^{13}$C NMR spectrum of imatinib mesylate Form IX in the 100-180 ppm range.
Figure 18:
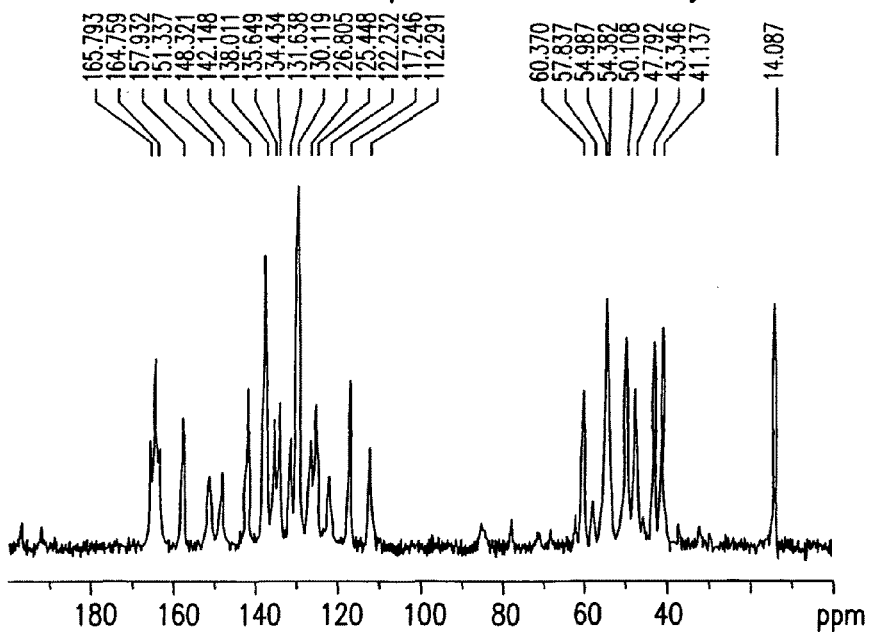
FIG. 18 illustrates a solid-state $^{13}$C NMR spectrum of imatinib mesylate Form IX.

Preferably, continuous stirring is performed during the crystallization process. Preferably, a solvent in which imatinib mesylate is insoluble is added during crystallization. Preferably, the solvent in which imatinib mesylate is insoluble is selected from a group consisting of: ether and aliphatic hydrocarbon. Preferably, the ether is a higher alkylether, such as methyl tertbutylether, diisopropylether and diisobutylether. Preferably, the aliphatic hydrocarbon is hexane or heptane The obtained imatinib mesylate Form VIII may then be recovered by any means known in the art such as by filtering, washing and drying The present invention provides crystalline imatinib mesylate, designated Form IX, characterized by data selected from the group consisting of: a powder XRD pattern with peaks at about 10.4, 14.8, 18.2, and 24.7±0.2 degrees two-theta; a powder XRD pattern depicted in FIG. 16; a solid-state $^{13}$C NMR spectrum with signals at about 157.9, 151.3 and 148.3±0.2 ppm; a solid-state $^{13}$C NMR spectrum having differences in chemical shifts between the signal exhibiting the lowest chemical shift and another in the chemical shift range of 100 to 180 ppm of about 45.6, 39.0, 36.0±0.1 ppm; a solid-state $^{13}$C NMR spectrum depicted in FIG. 17; and a solid-state $^{13}$C NMR spectrum depicted in FIG. 18. The signal exhibiting the lowest chemical shift in the chemical shift range of 100 to 180 ppm is, typically, at about 112.3±1 ppm.

In addition, this crystalline imatinib mesylate may be further characterised by data selected from the group consisting of: a solid-state $^{13}$C NMR spectrum having signals at about 142.1 and 138.0±0.2 ppm; and a solid-state $^{13}$C NMR spectrum having chemical shift differences between the peak exhibiting the lowest chemical shift and another in the chemical shift range of 100 to 180 ppm of about 29.8 and 25.7±0.1 ppm.

Also, this crystalline imatinib mesylate may be further characterized by a solid-state $^{13}$C NMR having a chemical shift at about 14.1±0.2.

The above crystalline imatinib mesylate may contain about 1% by weight of water as measured by KF. Furthermore, this crystalline imatinib mesylate may contain less than 1% by weight of residual solvents other than water as measured by GC and by solid state $^{13}$CNMR.

The said crystalline imatinib mesylate can be an intermediate for other forms of Imatinib mesylate, such as form α. Also, the said form is characterized by a small particle size, of less than 100 microns, hence, the dissolution rate is expected to be very fast and therefore it should have a better bioavailability. Hence, this form is attractive for formulations.

The present invention further encompasses a process for preparing imatinib mesylate form IX by a process comprising providing a suspension including an imatinib mesylate solvate selected from a group consisting of: ethanol, isopropanol, dioxolane, tetrahydrofuran, and mixtures thereof, and an ether in which imatinib mesylate is insoluble to obtain a suspension; and maintaining the suspension at a temperature of about −30° C. to about 25° C.

Preferable the starting imatinib mesylate solvated form can be form IV or V.

The ether in which imatinib mesylate is insoluble is preferably a $C_{2-6}$ ether, more preferably, tetrahydrofuran, methyltertbutyl ether, diisopropylether and diisobutylether, most preferably, methyltertbutyl ether. As one skilled in the art will appreciate, the time required to obtain Form IX will vary depending upon, among other factors, the polymorphic stability of a particular solvate, temperature, stoichiometric content of a solvent in a solvate, and the solvent polarity, and can be determined by taking periodic PXRD reading.

The suspension including the starting imatinib mesylate solvate and an ether in which imatinib mesylate is insoluble may be prepared by a process comprising: providing a suspension of imatinib base and tetrahydrofuran; admixing methanesulfonic acid; and maintaining to obtain imatinib mesylate. Preferably the tetrahydrofuran is substantially free of peroxides. Peroxides may be removed by any means known to the skilled artisan including for example by filtration through basic alumina. Preferably, the methanesulfonic acid is in tetrahydrofuran. More preferably, the concentration of the methanesulfonic acid in the tetrahydrofuran is about 10% by weight. Preferably, maintaining is by stirring.

Preferably, maintaining the suspension is by continuous stirring. Preferably, the suspension is maintained at a temperature of about −20° C. to about 25° C., preferably about 0° C. to about 25° C., more preferably at a temperature of about 10° C. to about 25° C., most preferably of about 20° C. to about to 25° C., for a sufficient amount of time to obtain imatinib mesylate form IX. Preferably the period is from about 12 hours to about 24 hours, more preferably from about 16 hours to about 24 hours, most preferably for about 20 hours. The crystalline imatinib mesylate Form IX may then be recovered by any means known in the art such as by filtering, and washing, and drying. Preferably, drying is at a temperature of about 60° C. to about 90° C. Preferably, the drying is with nitrogen, more preferably, under reduced pressure, most preferably in vacuum.

Figure 19:
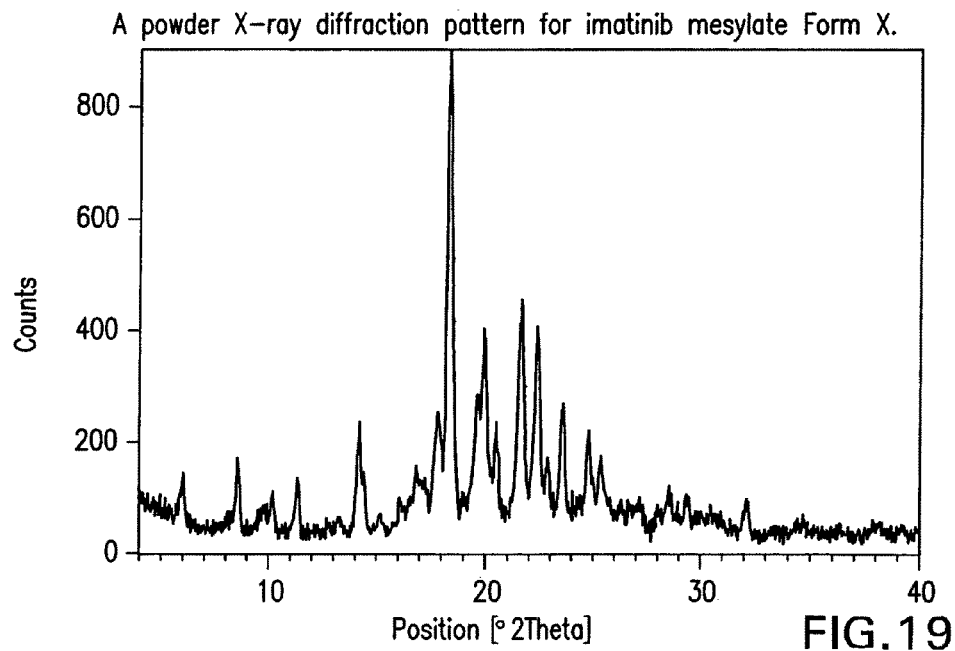
FIG. 19 illustrates a powder X-ray diffraction pattern for imatinib mesylate Form X.
Figure 20:
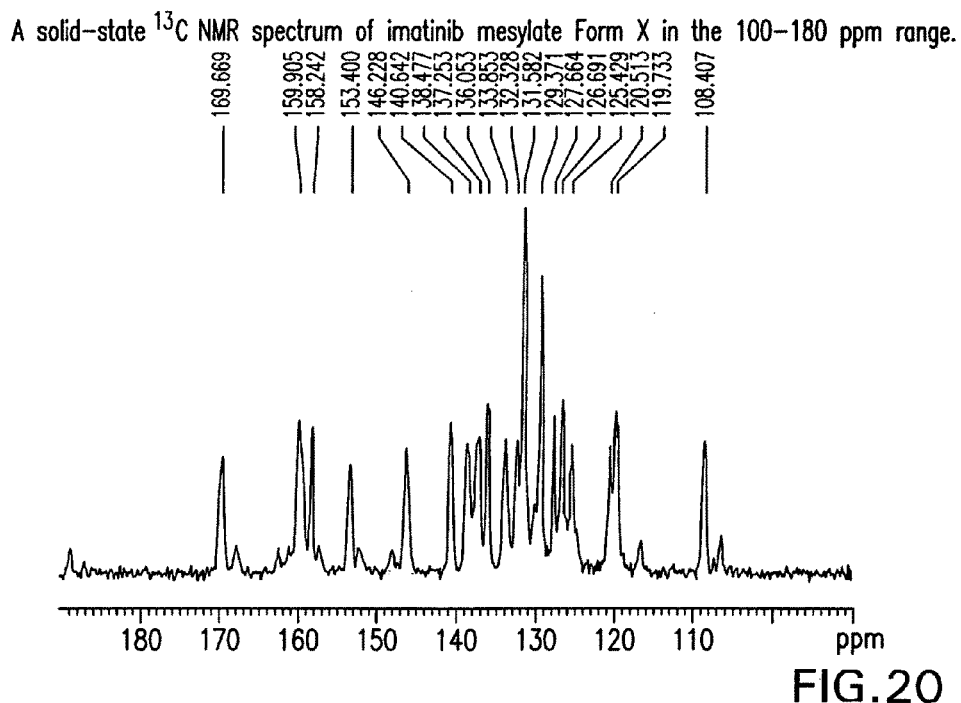
FIG. 20 illustrates a solid-state $^{13}$C NMR spectrum of imatinib mesylate Form X in the 100-180 ppm range.
Figure 21:
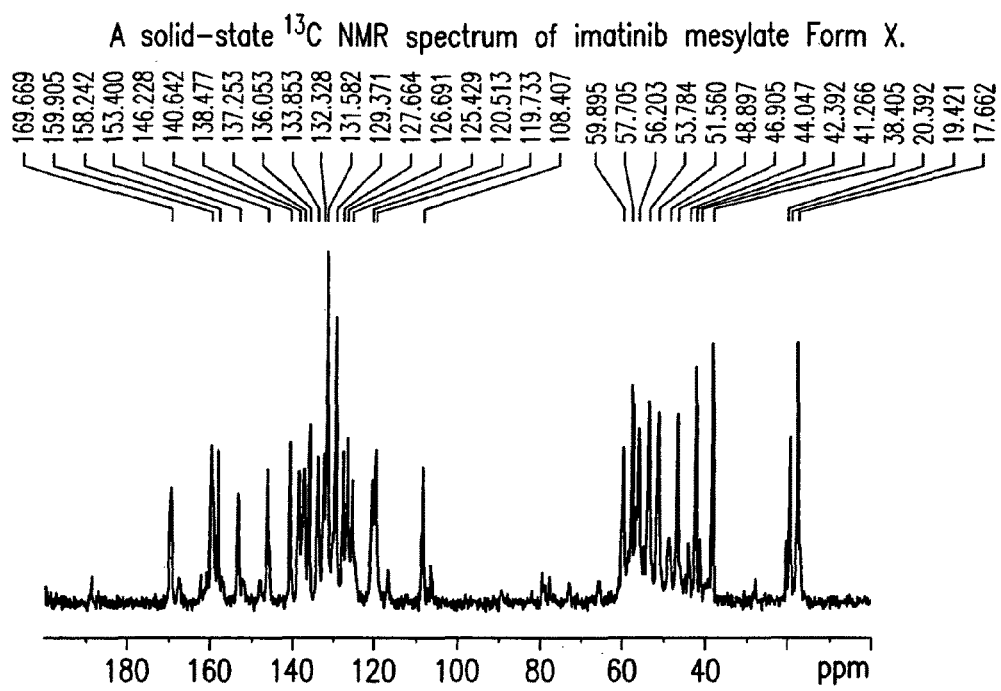
FIG. 21 illustrates a solid-state $^{13}$C NMR spectrum of imatinib mesylate Form X.

The present invention provides crystalline imatinib mesylate, designated imatinib mesylate Form X, characterised by data selected from the group consisting of: a powder XRD pattern with peaks at about 6.0, 8.6, 11.4, 14.2, 18.3±0.2 degrees two-theta; a powder XRD pattern having peaks at about: 6.0, 8.6, 10.2, 11.4, 14.2, ±0.2 degrees two-theta; a powder XRD pattern having at least five peaks selected from the list consisting of peaks at about: 6.0, 8.6, 10.2, 11.4, 14.2, 17.8, 18.3, 21.6, 22.4, 23.6, 24.8±0.2 degrees two-theta; a powder XRD pattern depicted in FIG. 19; a solid-state $^{13}$C NMR spectrum with signals at about 159.9, 158.2 and 153.4±0.2 ppm; a solid-state $^{13}$C NMR spectrum having chemical shift differences between the signal exhibiting the lowest chemical shift and another in the chemical shift range of 100 to 180 ppm of about 51.5, 49.8, and 45.0±0.1 ppm; a solid-state $^{13}$C NMR spectrum depicted in FIG. 20; and a solid-state $^{13}$C NMR spectrum depicted in FIG. 21. The signal exhibiting the lowest chemical shift in the chemical shift range of 100 to 180 ppm is, typically, at about 108.4±1 ppm.

The above crystalline imatinib mesylate may be further characterised by data selected from the group consisting of: a powder XRD pattern having peaks at about 19.9, 20.5, 21.6 and 22.4±0.2 degrees two-theta, a powder XRD pattern having peaks at about: 10.2, 20.5 and 21.6±0.2 degrees two-theta; a solid-state $^{13}$C NMR spectrum having signals at about 146.2, 140.6±0.2 ppm; and a solid-state $^{13}$C NMR spectrum having chemical shift differences between the signal exhibiting the lowest chemical shift and another in the chemical shift range of 100 to 180 ppm of about 37.8 and 32.2±0.1 ppm.

In addition, this crystalline imatinib mesylate may be further characterized by a solid-state $^{13}$C NMR spectrum having signals at about 19.4 and 17.7±0.1 ppm.

The above crystalline imatinib mesylate is an ethanol solvate of imatinib mesylate. Preferably, the crystalline form may contain about 6% to about 10%, more preferably about 7% to about 8% by weight of ethanol as measured by GC. The crystalline form also contains up to 6% by weight of water, as measured by KF. Furthermore, the presence of ethanol in the structure of the solvate can also be characterized by the presence of sharp signals at 19.4 ppm (methyl) and at 57.7 ppm (methyne) in the solid-state $^{13}$CNMR spectrum. The content of ethanol can be decreased down to 2% by weight, as measured by GC by drying or by heating.

Figure 33:
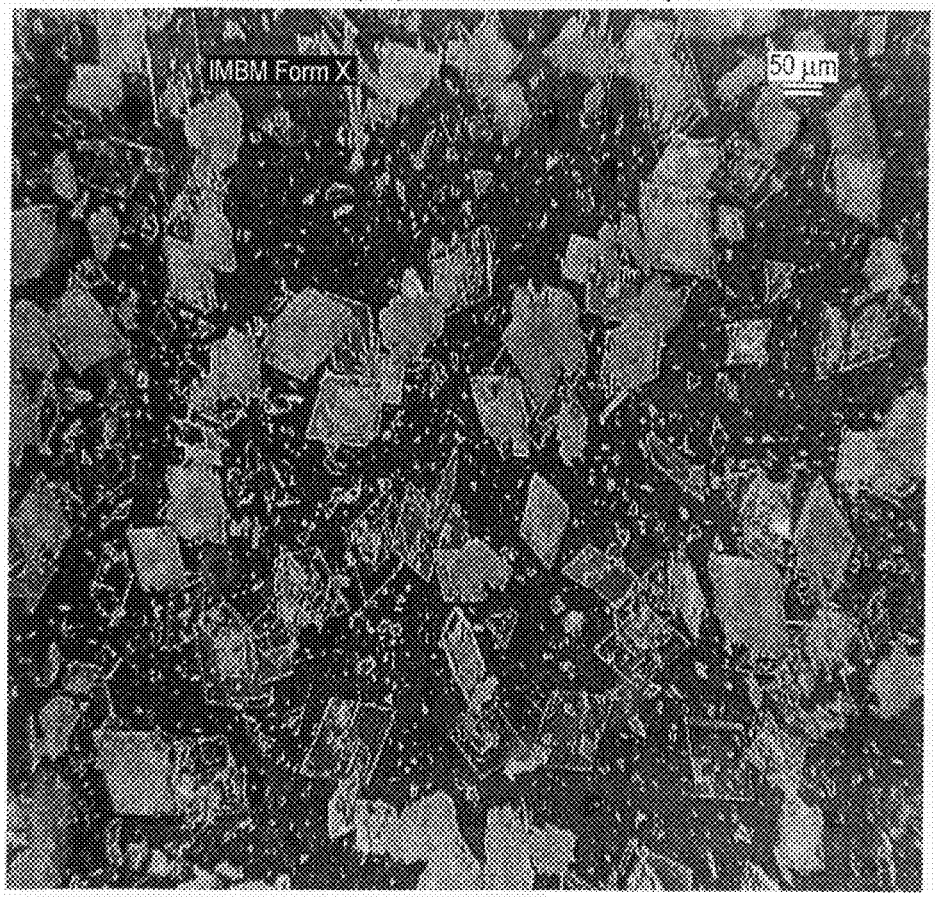
FIG. 33 illustrates an optical microscope photo of imatinib mesylate form X.
Figure 34:
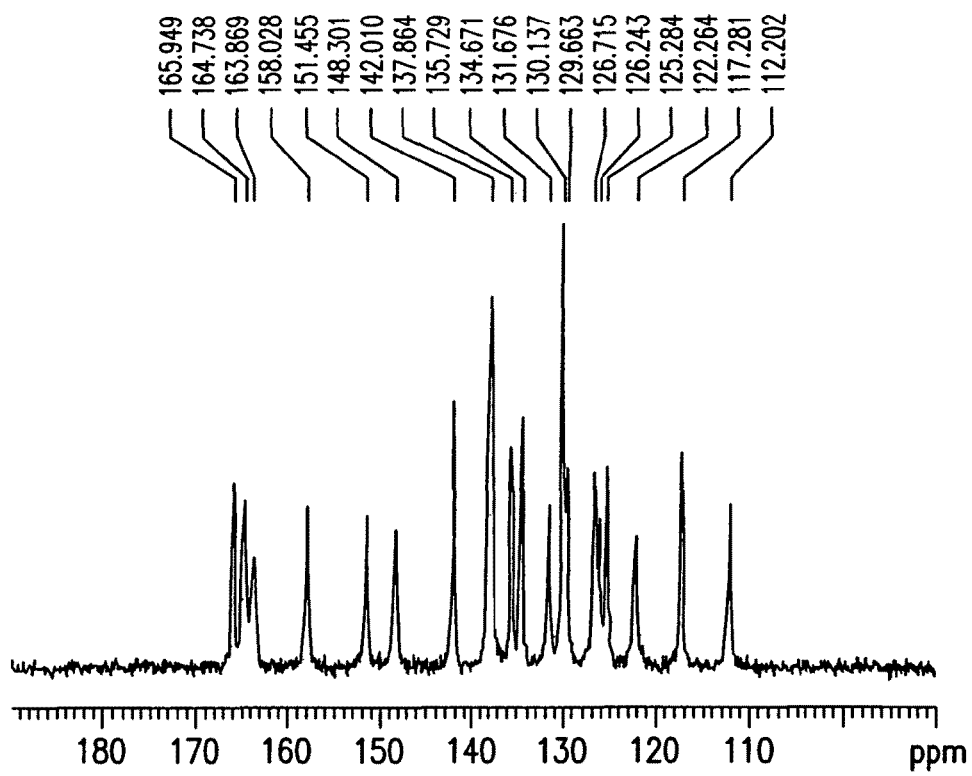
FIG. 34 illustrates a solid-state $^{13}$C NMR spectrum of form α in the 100-180 ppm range.
Figure 35:
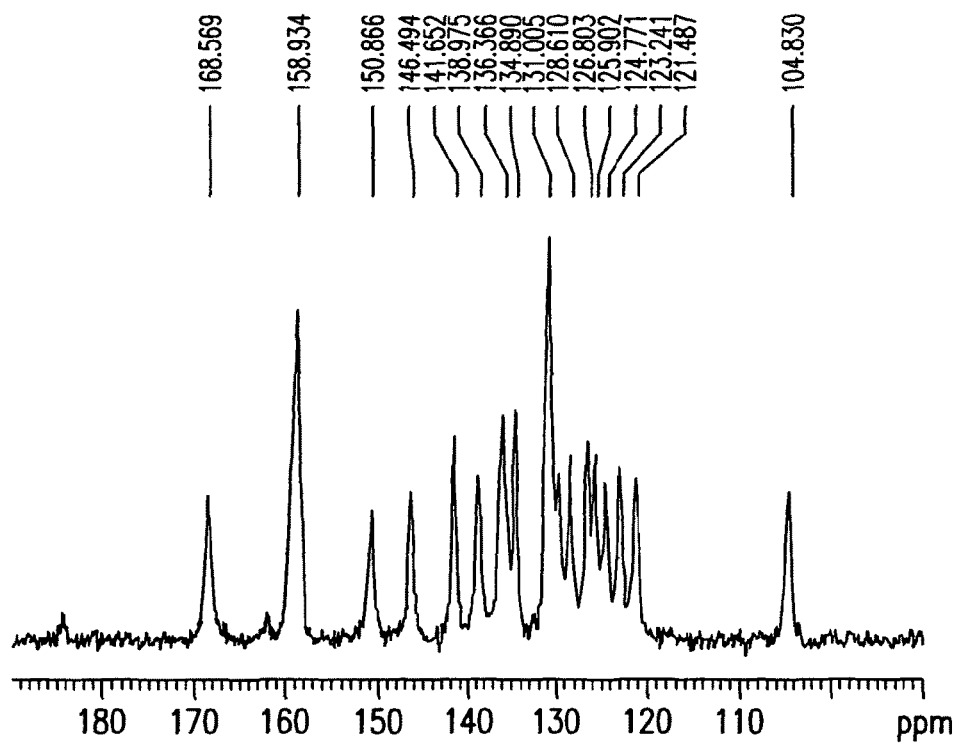
FIG. 35 illustrates a solid-state $^{13}$C NMR spectrum of form α in the 100-180 ppm range.

Also, the said crystalline imatinib mesylate has a surprisingly, regular rhomboidal particle shape, which distinguishes it from all other forms of Imatinib mesylate as shown in FIG. 33. Therefore, it is expected to have an excellent flowability. In addition, form X is provided having small crystals, with a particle size of less than 100 microns, having the same morphology as illustrated in FIG. 33. Thus, the excellent flowability properties can be retained even with such small particles. Thus, this form is exceptionally attractive for formulations.

The present invention further encompasses a process for preparing the imatinib mesylate Form X from by a process comprising: maintaining imatinib mesylate form IV at a temperature of about 20° C. to about 30° C.

Imatinib mesylate form IV can be dried before it is maintained to provide form X. Preferably, the drying is done at a temperature of about −5° C. to about −30° C. Preferably, Imatinib mesylate form IV is maintained at a temperature of about −5° C. to about −30° C. for about 6 to about 10 hours. Preferably, imatinib mesylate is maintained at a temperature of about 25° C. Preferably, the heating is for a time period of about 4 to about 48 hours, preferably for about 8 to about 24 hours, more preferably for about 10 hours. Although this process is preferably applied to 0.5 g to about 2 g of imatinib mesylate Form IV, the skilled artisan will know to calibrate the time periods accordingly. Preferably, the process is performed under nitrogen sweep.

The present invention further encompasses another process for preparing crystalline Imatinib mesylate form X comprising providing a solution of imatinib mesylate and a mixture of water and ethanol; and precipitating by maintaining the solution at a temperature of about 0° C. to about −30° C. to obtain a suspension comprising of imatinib mesylate form X.

The solution of imatinib mesylate in a mixture of water and ethanol is provided by combining imatinib base with ethanol providing a suspension; adding water providing a new suspension; cooling the new suspension; adding methanesulfonic acid to the cooled new suspension, and maintaining at a temperature of about −30° C. to about 0° C., preferably to about −5° C. to about −25° C., more preferably to about −5° C. to about −15° C. Preferably, the temperature to which the new suspension is cooled is the same temperature at which it is maintained, after the addition of methane sulfonic acid. Preferably, an ethanolic solution of methanesulfonic acid is added. Typically, after the addition of methanesulfonic acid a mixture comprising is obtained. This mixture is maintained to allow complete formation of Imatinib mesylate. The indication for a complete reaction is when all the solid dissolves.

Optionally, seeding of the solution can be done.

Usually, the solution is maintained at low temperatures providing a precipitate of the said crystalline form. First, the solution is maintained at a temperature of about −10° C. to about 0° C., preferably at about −5° C., for about 1 hour to about 4 hours, preferably for about 3 hours to about 4 hours, more preferably for about 190 minutes, and then, at temperature of about −30° C. to about −15° C., preferably at about −30° C. to about −20° C., more preferably at about −27° C. for a period of about 2 hours to about 18 hours, preferably of about 6 hours to about 16 hours, more preferably 12 hours.

Optionally, a second solvent in which imatinib mesylate isn't soluble can be added to the suspension comprising of the crystalline form. This solvent is used to avoid dissolution of imatinib mesylate.

The process for preparing form X can further comprise recovering the said crystalline form. The recovery can be done by any method known to a skilled artisan. Preferably, the recovery is done by filtering the suspension, washing the filtered product and drying it.

The present invention further encompasses another process for preparing crystalline Imatinib mesylate form X comprising providing a suspension of imatinib mesylate form V and ethanol.

The suspension is prepared by combining imatinib mesylate form V and ethanol at a temperature of about 25° C. Typically, the suspended form V transforms to form X, which can then be recovered. The recovery may be done by any method known in the art, such as filtering the suspension, washing and drying.

Figure 22:
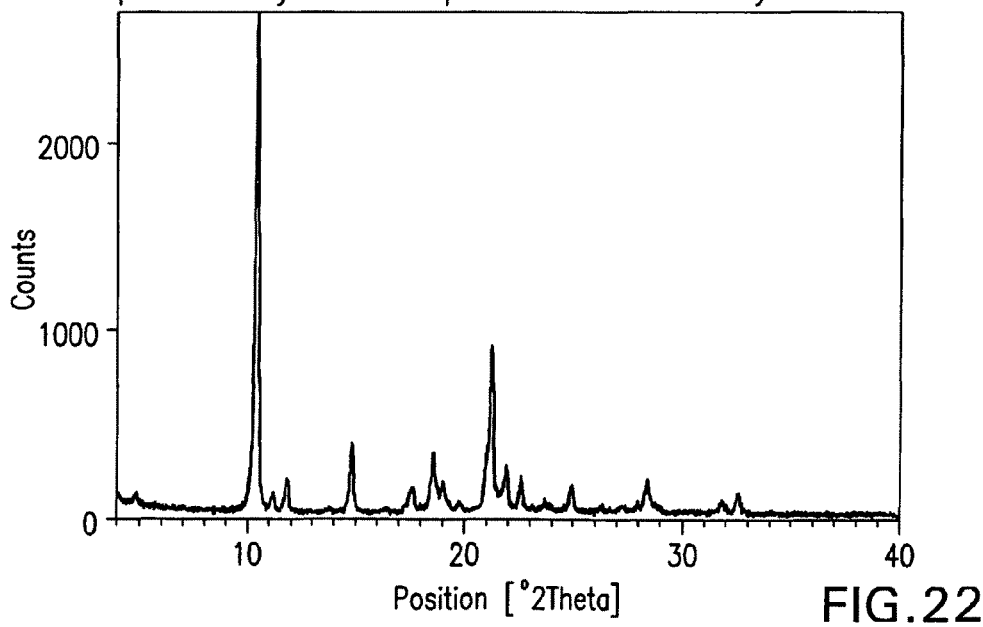
FIG. 22 illustrates a powder X-ray diffraction pattern for imatinib mesylate Form XI.

The present invention provides crystalline imatinib mesylate, designated imatinib mesylate Form XI, characterised by data selected from the group consisting of: a powder XRD pattern with peaks at about 10.4, 11.2, 11.8, 14.8 and 21.2±0.2 degrees two-theta; a powder XRD pattern with peaks at about 10.4, 14.8, 18.6, and 21.2±0.2 degrees two-theta; a powder XRD pattern having peaks at about: 10.4, 11.8, 14.8, and 18.6±0.2 degrees two-theta; a powder XRD pattern having at least five peaks selected from the list consisting of peaks at about: 10.4, 11.2, 11.8, 14.8, 18.6, 21.9, 22.6, 24.9±0.2 degrees two-theta; a PXRD pattern depicted in FIG. 22.

This crystalline imatinib mesylate may be further characterized by data selected from the group consisting of: a powder XRD pattern with peaks at about 18.6, 19.0, 21.9, and 22.6±0.2 degrees two-theta; and a powder XRD pattern having peaks at about: 21.2, and 21.6±0.2 degrees two-theta.

The said crystalline imatinib mesylate can be an intermediate for other forms of Imatinib mesylate, such as form α. Also, the said form is characterized by a small particle size, of less than 100 microns, hence, the dissolution rate is expected to be very fast and therefore it should have a better bioavailability. Hence, this form is attractive for formulations.

The present invention further encompasses a process for preparing the imatinib mesylate form XI by a process for comprising: providing a solution of imatinib mesylate and tetrahydrofuran; and crystallizing to obtain imatinib mesylate form XI.

The solution of imatinib mesylate is prepared by a process comprising: providing a suspension of imatinib base and tetrahydrofuran; admixing methanesulfonic acid; and maintaining to obtain imatinib mesylate. A suitable concentration of imatinib mesylate in tetrahydrofuran preferably can range from about 1:5 to about 1:30 in weight (g) imatinib mesylate to volume (ml) ethanol. Preferably the tetrahydrofuran is substantially free of peroxides. Peroxides may be removed by any means known to the skilled artisan including for example by filtration through basic alumina. Preferably, the methanesulfonic acid is in tetrahydrofuran. More preferably, the concentration of the methanesulfonic acid in the tetrahydrofuran is about 10% by weight. Preferably, maintaining is by stirring.

Preferably, crystallization is by maintaining the solution at a temperature below 30° C., more preferably, between about −30° C. to about 20° C., even more preferably between 0° C. to about 110° C. The crystalline imatinib mesylate Form XI may then be recovered by any means known in the art such as by filtering, and washing, however excessive drying will likely result in Form IX.

Figure 23:
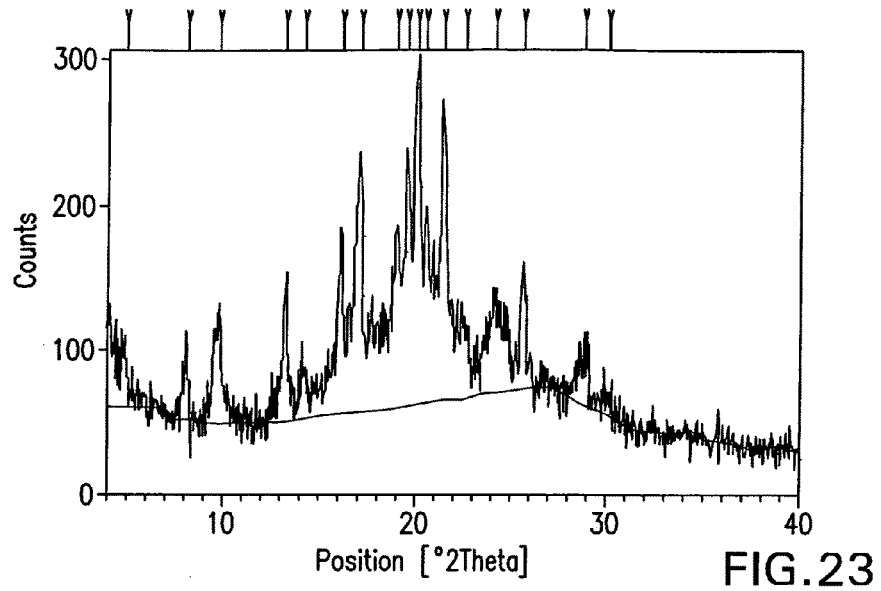
FIG. 23 illustrates a powder X-ray diffraction pattern for imatinib mesylate composition containing amorphous form and crystalline form IV.

The present invention provides a composition of amorphous form and crystalline form of imatinib mesylate, designated imatinib mesylate Form IV. This composition is characterized by data selected from the group consisting of: a powder XRD pattern with peaks at about 8.1, 9.7, 13.2, 16.1, and 17.0±0.2 degrees two-theta, and a PXRD pattern depicted in FIG. 23.

The above composition comprises amorphous imatinib mesylate and form IV in a ratio of about 1 to 1, as measured by PXRD.

The above composition may contain less than 1% by weight of ethanol, as measured by GC.

The present invention further encompasses a process for preparing the above composition of imatinib mesylate comprising: suspending imatinib mesylate Form IV in an aliphatic hydrocarbon, and heating the suspension to a temperature of about 40° C. to about 100° C. to obtain the said composition.

Preferably, the heating is to a temperature of about 60° C. to about 90° C., more preferably to about 80° C. More preferably, the aliphatic hydrocarbon used is a $C_{5-8}$ aliphatic hydrocarbon, especially n-heptane, n-hexane, n-octane, or cyclohexane. The process may comprise a recovery step. Recovery of the crystalline imatinib mesylate is preformed by any means known in the art such as by filtering, washing and drying. Preferably, the washing is with petrolether.

The present invention provides another process for preparing the above composition comprising heating Imatinib mesylate Form IV to a temperature of about 40 C to about 100° C. providing the above composition.

Preferably, the heating is done at a temperature of about 50° C. to about 80° C. Preferably, the heating is done for about 2 to about 24 hours, more preferably, for about 4 to about 12 hours.

Figure 24:
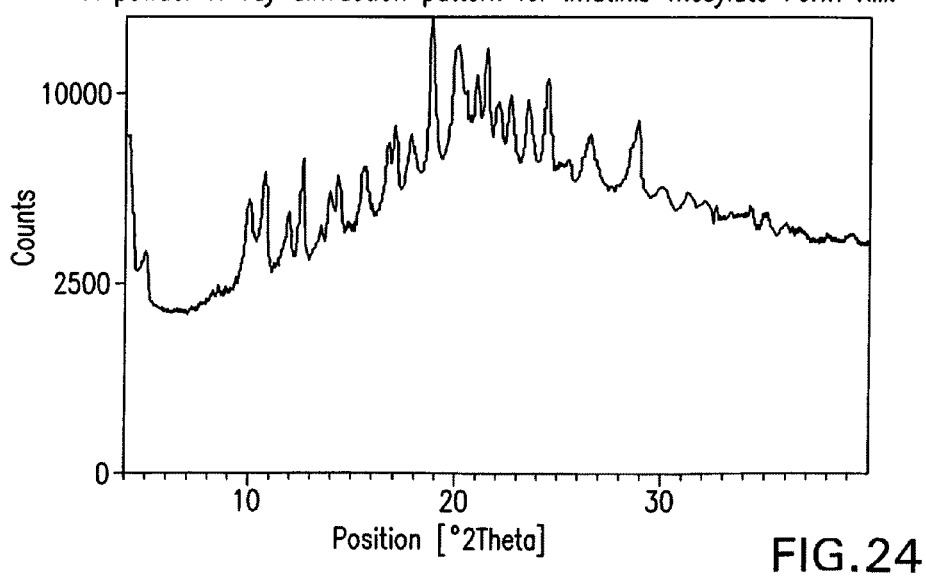
FIG. 24 illustrates a powder X-ray diffraction pattern for imatinib mesylate Form XIII.

The present invention provides crystalline imatinib mesylate, designated imatinib mesylate Form XIII, characterized by data selected from the group consisting of: a powder XRD pattern with peaks at about 10.0, 10.8, 11.9, 12.6 and 18.8±0.2 degrees two-theta; a powder XRD pattern with peaks at about 10.0, 10.8, 12.6 and 14.3±0.2 degrees two-theta; a powder XRD pattern having peaks at about: 10.0, 10.8, 12.0, 12.6, and 16.7±0.2 degrees two-theta; a powder XRD pattern having at least five peaks selected from the list consisting of peaks at about: 10.0, 10.8, 11.9, 12.6, 14.3, 15.6, 17.1, 18.8, 22.7, 23.6, 24.4±0.2 degrees two-theta; and a PXRD pattern depicted in FIG. 24.

This crystalline imatinib mesylate may be further characterized by data selected from the group consisting of: a powder XRD having peaks at about 16.7, 21.0, 21.5, 23.6, and 24.4±0.2 degrees two-theta, and a powder XRD pattern having peaks at about 18.8, and 24.4±0.2 degrees two-theta.

In addition, the above crystalline imatinib mesylate contains less than 1% by weight of ethanol, as measured by GC. Also, it also contains up to 2% by weight of water, as measured by KF.

The present invention further encompasses a process for preparing the imatinib mesylate Form XIII comprising heating Form IV to a temperature of about 40° C. to about 100° C., more preferably to a temperature of about 50° C. to about 70° C., most preferably to a temperature of about 60° C. Preferably, heating is done under inert atmosphere condition such as nitrogen stream. As one skilled in the art will appreciate, the time required to obtain imatinib mesylate Form XIII will vary depending upon, among other factors, the amount of starting Form IV and the heating temperature, and can be determined by taking periodic PXRD readings.

Figure 25:
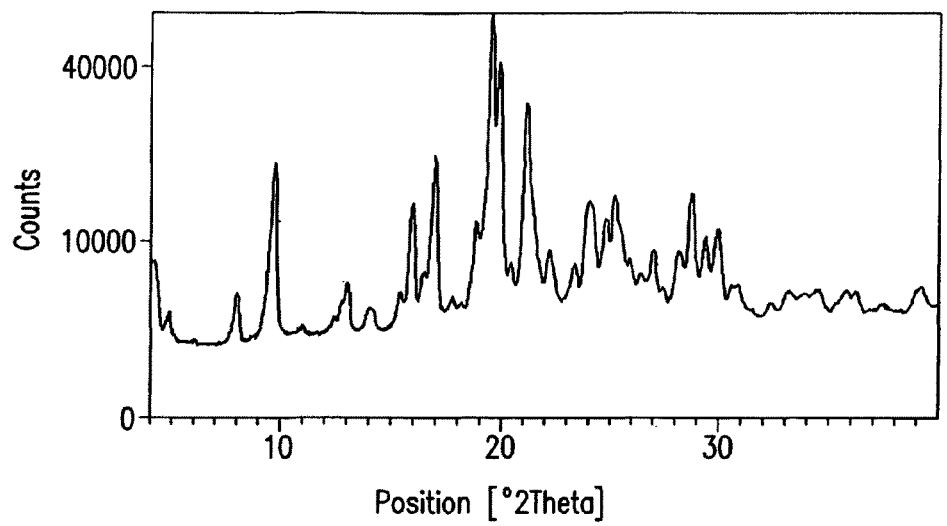
FIG. 25 illustrates a powder X-ray diffraction pattern for imatinib mesylate Form XIV.

In yet another embodiment, the present invention provides crystalline imatinib mesylate, designated imatinib mesylate Form XIV, characterized by data selected from the group consisting of: a powder XRD pattern with peaks at about 9.7, 16.0, 17.0, 19.5, 21.1, and 25.2±0.2 degrees two-theta; a powder XRD pattern having peaks at about: 8.0, 9.7, 21.1, and 25.2±0.2 degrees two-theta; and PXRD pattern depicted in FIG. 25.

In addition, this crystalline imatinib mesylate may be further characterized by a powder XRD pattern having a peak at about 29.4±0.2 degrees two-theta.

The above crystalline imatinib mesylate is an isopropanol solvate of imatinib mesylate. Preferably, the crystalline form contains about 7% to about 11%, more preferably about 9% by weight of isopropanol as measured by GC.

Also, the said imatinib mesylate is characterized by a small particle size, of less than 100 microns, hence, the dissolution rate is expected to be very fast and therefore it should have a better bioavailability. Hence, this form is attractive for formulations.

The present invention further encompasses a process for preparing imatinib mesylate form XIV comprising: providing a solution of imatinib mesylate, in a mixture of isopropanol and water; and cooling the solution to obtain a suspension comprising of imatinib mesylate form XIV, wherein the water content in the mixture of isopropanol and water is of about 10% to about 20% by weight.

The solution of imatinib mesylate in a mixture of isopropanol and water is prepared by a process comprising: providing a suspension of imatinib base, isopropanol and water; admixing the suspension with methanesulfonic acid to obtain a mixture; and maintaining the mixture at a temperature of about −20° C. to about 0° C., preferably about −5° C., to obtain a solution of imatinib mesylate.

Preferably, the mixture of isopropanol and water contains about 12% by weight of water. Preferably, methanesulfonic acid is added to the suspension at a temperature of about 0° C. to about −10° C., more preferably at a temperature of about −5° C. Preferably, after adding the methanesulfonic acid the mixture is kept at the same temperature for a period of about 10 minutes to about 1 hour, preferably for about 20 minutes to about 30 minutes, more preferably for about 20 minutes. Preferably, the solution is maintained at a temperature of about 0° C. to about −20° C., more preferably, at a temperature of about −15° C. Preferably, the solution is maintained for a period of about 10 hours to about 24 hours, preferably overnight.

Alternatively, the solution of imatinib mesylate in a mixture of isopropanol and water is prepared by a process comprising: suspending imatinib mesylate in a mixture of isopropanol and water, and heating the suspension to obtain a solution. Preferably, the heating is to a temperature of about 30° C. to about reflux, preferably of about 60° C. to about 83° C. Preferably, the mixture of isopropanol and water contains about 12% by weight of water. A suitable concentration of imatinib mesylate in isopropanol water mixture preferably can range from about 1 g of imatinib mesylate per 5 ml of solvent mixture to about 1 g of imatinib mesylate per 30 ml of solvent mixture.

Preferably, the cooling is temperature to about 0° C. to about −20° C., more preferably, to about −15° C. Preferably, continuous stirring is performed during the precipitation process. Preferably, a solvent in which imatinib mesylate is insoluble can be added during crystallization. A solvent in which imatinib mesylate is insoluble is preferably selected from the group consisting of: ethers and aliphatic hydrocarbons. Preferably, the ether is a higher alkylether, such as methyl tertbutylether, diisopropylether and diisobutylether. Preferably, the aliphatic hydrocarbon is hexane or heptane. The obtained imatinib mesylate Form XIV may then be recovered by any means known in the art such as by filtering, washing and drying.

Figure 26:
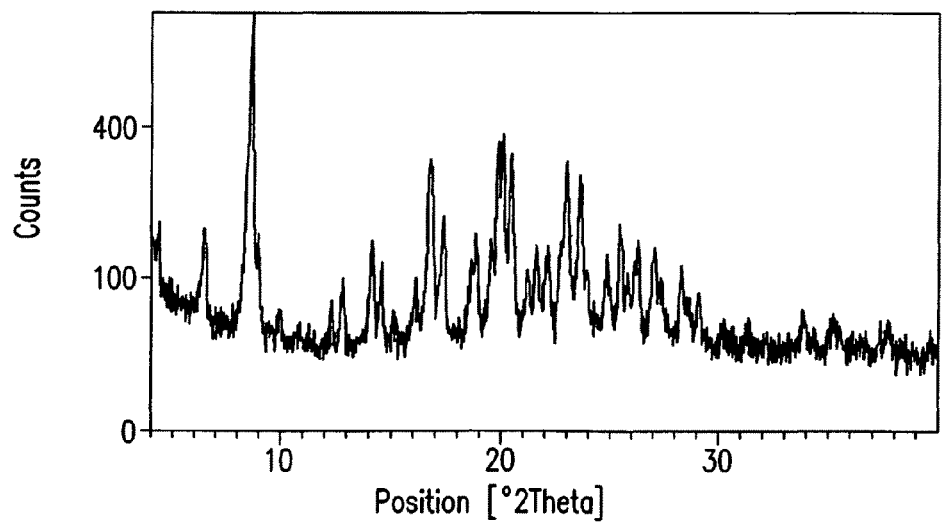
FIG. 26 illustrates a powder X-ray diffraction pattern for imatinib mesylate Form XV.
Figure 27:
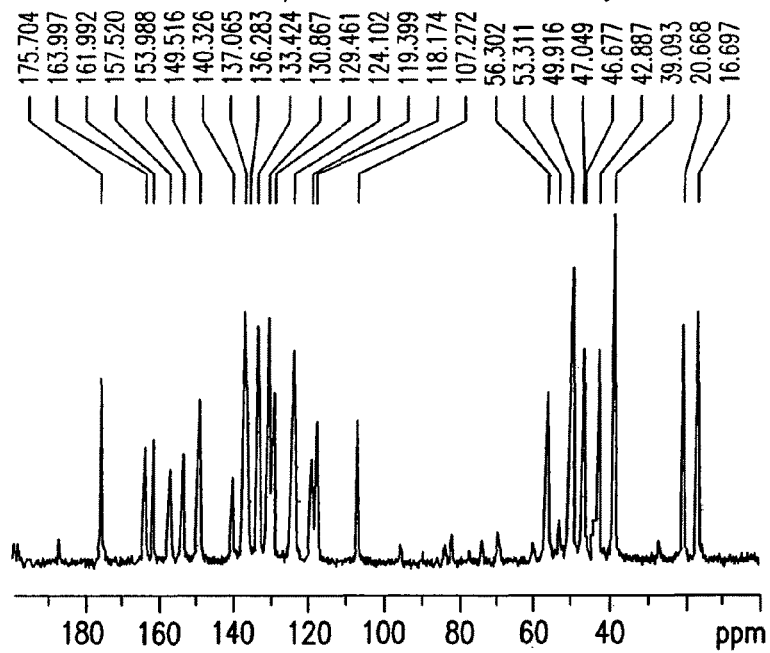
FIG. 27 illustrates a solid-state $^{13}$C NMR spectrum of imatinib mesylate Form XV.
Figure 28:
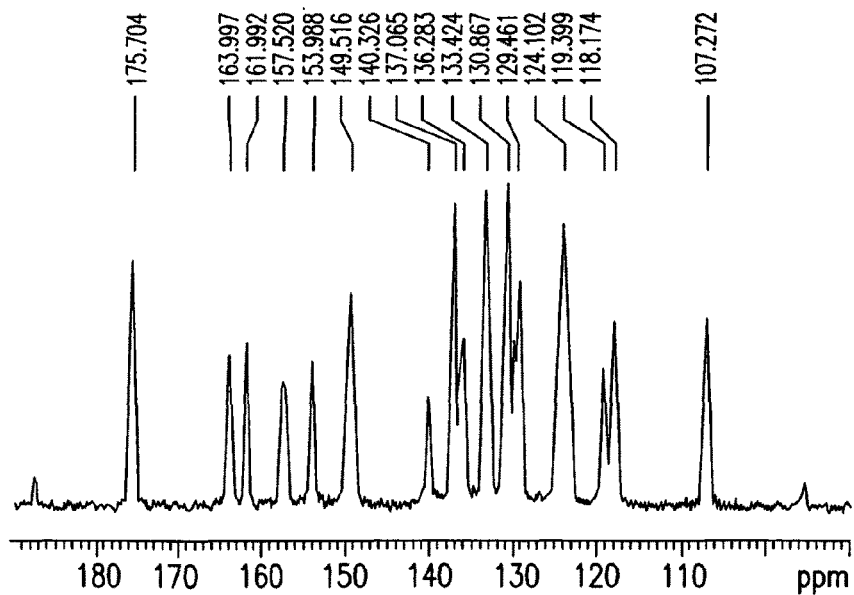
FIG. 28 illustrates a solid-state $^{13}$C NMR spectrum of imatinib mesylate Form XV in the 100-180 ppm range.

The present invention provides crystalline imatinib mesylate, designated imatinib mesylate Form XV, characterized by data selected from the group consisting of: a powder XRD pattern with peaks at about 6.5, 8.6, 14.1, 16.7, and 17.3±0.2 degrees two-theta; a powder XRD pattern with peaks at about 6.5, 8.6, 14.1, and 16.7±0.2 degrees two-theta; a powder XRD pattern depicted in FIG. 26; a powder XRD pattern having at least five peaks selected from a list consisting of peaks at about: 6.5, 8.6, 14.1, 16.7, 17.3, 22.9, 23.6, 25.4, 26.2±0.2 degrees two-theta a solid-state $^{13}$C NMR spectrum with signals at about 162.0, 164.0, and 157.5±0.2 ppm; a solid-state $^{13}$C NMR spectrum having chemical shift differences between the signal exhibiting the lowest chemical shift and another in the chemical shift range of 100 to 180 ppm of about 56.7, 54.7, and 50.2±0.1 ppm; a solid-state $^{13}$C NMR spectrum depicted in FIG. 27, and a solid-state $^{13}$C NMR spectrum depicted in FIG. 28. The signal exhibiting the lowest chemical shift in the chemical shift range of 100 to 180 ppm is, typically, at about 107.3±1 ppm.

The said crystalline imatinib mesylate may be further characterized by data selected from the group consisting of: a powder XRD pattern having peaks at about 19.8, 20.1, 23.0, and 23.6±0.2 degrees two-theta; a powder XRD pattern having peaks at about 19.8, and 23.0±0.2 degrees two-theta; and a solid-state $^{13}$C NMR having signals at about 140.3, 149.5, and 154.0±0.2 ppm.

In addition this crystalline imatinib mesylate may be further characterized by a solid-state $^{13}$C NMR signal at 16.7±0.2 ppm.

The above crystalline imatinib mesylate is a mono-solvate of acetic acid of imatinib mesylate. Preferably, the acetic acid ratio vs. imatinib mesylate is of about 1:1, as measured by solution $^1$H NMR analysis. Furthermore, the presence of acetic acid in the structure of the solvate can also be characterized by the presence of sharp signals at 20.7 ppm (methyl) and at 175.7 ppm (carbonyl) in the solid-state $^{13}$C NMR spectrum.

Also, the said crystalline imatinib mesylate is characterized by a small particle size, of less than 100 microns, hence, the dissolution rate is expected to be very fast and therefore it should have a better bioavailability. Hence, this form is attractive for formulations.

The present invention further encompasses a process for preparing the imatinib mesylate Form XV comprising providing a solution of imatinib mesylate comprising acetic acid, and admixing the solution with an organic solvent able to precipitate imatinib mesylate to obtain a suspension comprising imatinib mesylate Form XV.

A suitable concentration of imatinib mesylate in acetic acid is 1 g of imatinib mesylate per 3 ml of acetic acid to about 1 g of imatinib mesylate per 30 ml of acetic acid, preferably of about 1 g of imatinib mesylate per 5 ml of acetic acid.

Alternatively, the solution may be prepared by combining imatinib base, methanesulfonic acid, and acetic acid. Preferably, imatinib base is dissolved in acetic acid and than methanesulfonic acid is added. Alternatively, imatinib base can be dissolved or suspended in an organic solvent comprising acetic acid is added, and then methanesulfonic acid is added.

When the combination of imatinib base and the solvent provides a suspension, the addition of acetic acid aids in dissolution.

Preferably, suitable organic solvents that are able to precipitate imatinib mesylate can be one of, but are not limited to, esters of organic acids, such as ethylacetate, propylacetate, butylacetate, isopropylacetate, or isobutylacetate, and ethers, such as tert-butyl methyl ether. More preferably, the organic solvent is butylacetate.

Cooling the suspension may be carried out to increase the yield of the precipitated product. Preferably, cooling is to a temperature of about 10° C. to about −30° C., more preferably, to a temperature of about 0° C. to about −15° C., more preferably to about 0° C. Preferably, the cooling is done without stirring. Optionally, during precipitation, a solvent in which is imatinib mesylate is insoluble can be added in order improve the yield of crystallization. The solvent can be picked from the above list.

The process for preparing the above crystalline form can further comprise a recovery process. The recovery may be performed by any means known in the art such as by filtering, washing and drying. Preferably the drying is provided under a nitrogen stream.

Figure 29:
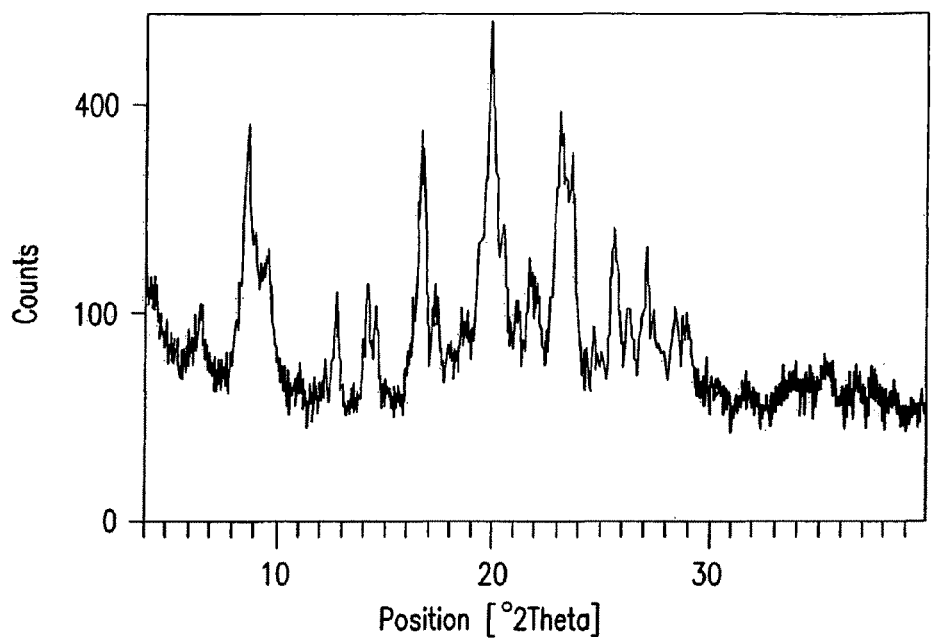
FIG. 29 illustrates a powder X-ray diffraction pattern for imatinib mesylate Form XVI.

The present invention provides crystalline imatinib mesylate, designated Form XVI, characterized by a powder XRD pattern with peaks at about 6.5, 8.7, 12.7, 14.2 and 16.7±0.2 degrees two-theta; and a powder XRD pattern depicted in FIG. 29.

This said crystalline imatinib mesylate may be further characterized by a powder XRD pattern having peaks at about 19.8 and 23.1±0.2 degrees two-theta.

The above crystalline imatinib mesylate may be a hemisolvate of acetic acid. Preferably, the acetic acid ratio vs. imatinib mesylate is of about 0.5:1 as measured by solution $^1$HNMR analysis.

Also, the said crystalline is characterized by a small particle size, of less than 100 microns, hence, the dissolution rate is expected to be very fast and therefore it should have a better bioavailability. Hence, this form is attractive for formulations.

The present invention further encompasses a process for preparing the imatinib mesylate Form XVI comprising heating imatinib mesylate Form XV to obtain imatinib mesylate Form XVI.

Preferably, imatinib mesylate Form XV is heated to the temperature of about 30° C. to about 120° C., more preferably to a temperature of about 60° C. Optionally, imatinib mesylate Form XV is heated under a stream of gas, or reduced pressure or combination thereof.

In addition, the present invention provides the above forms of imatinib mesylate, designated, form IV, V, VI, VII, VIII, IX, X, XI, XIII, XIV, XV and XVI having not more than 10%, more preferably not more than 5%, most preferably not more than 1% by weight of imatinib mesylate forms alpha, or beta. The purity of the above crystalline forms can be measured by PXRD using peak of form alpha when measuring the content of form alpha or by using peaks of form beta when measuring the content of form beta. When measuring the content of form a the peaks may be selected from the following list of peaks at about: 5.0, 10.5, 12.0, 15.0, 16.6, 17.8, 18.1, 18.7, 19.1, 21.4, 21.7±0.2 degrees two theta; and when measuring the content of form beta, the peaks may be selected from the following list of peaks at about: 9.7, 11.0, 11.7, 13.9, 14.7, 15.7, 17.5, 18.2, 20.0, 20.6, 21.1, 22.1, 22.7 and 23.8°±0.2 degrees two theta.

Alternatively, the purity of the above crystalline forms can be measured by solid-state $^{13}$CNMR using peak of form alpha when measuring the content of form a or by using signals of form β when measuring the content of form β. When measuring the content of form α the signals may be selected from the following list of signals at about: 165.9, 164.7, 158.0, 151.5, 142.0, 137.9, 135.7, 134.7, 131.7, 130.1, 129.7, 126.7, 126.2, 125.3, 117.3, 112.2 ppm±0.2 ppm, and when measuring the content of form β, the signals are selected from the following list of signals at about: 168.6, 158.9, 150.9, 146.5, 141.7, 139.0, 136.4, 134.9, 131.0, 128.6, 126.8, 125.9, 124.8, 123.2, 121.5, 104.8 ppm±0.2 ppm.

The present invention further encompasses a process for preparing crystalline imatinib mesylate Form α by crystallizing Imatinib mesylate from a solution of imatinib mesylate in a solvent selected from the group consisting of: 1,2-propylene carbonate, a mixture of n-propanol, and acetic acid, and mixtures thereof.

The solution of imatinib mesylate and 1,2-propylene carbonate is prepared by dissolving imatinib mesylate in 1,2-propylene carbonate at a temperature of about 50° C. to about 90° C., preferably of about 60° C. to about 80° C. When a mixture of n-propanol and acetic acid is the solvent, the solution is provided by combining imatinib mesylate or imatinib base and a mixture of isopropanol and acetic acid providing a suspension, and heating the suspension to obtain a solution; wherein when imatinib base is the starting material the process comprises the addition of methanesulfonic acid after obtaining the solution. Preferably, the suspension is heated to a temperature of about 30° C. to about 100° C., more preferably to about 40° C. to about 80° C., even more preferably to about 70° C.

Typically, the crystallization includes precipitating the said crystalline form from the solution. The precipitation can be induced by cooling the solution, by concentrating the solution or by combination thereof. Preferably, cooling is to a temperature of about 30° C. to about 0° C., more preferably to a temperature of about 10° C. to about 0° C.

As one skilled in the art will appreciate, the time required to obtain Form α imatinib mesylate will vary depending upon, among other factors, the amount of precipitate to be cooled and the cooling temperature, and can be determined by taking periodic XRD readings. Recovery of imatinib mesylate Form α is performed by any means known in the art such as by filtering, washing and drying. Preferably, the drying is at a temperature of about 60° C. to about 80° C., more preferably in a vacuum.

The present invention encompasses a process for preparing crystalline imatinib mesylate Form α by providing a solution of Imatinib mesylate in ethyleneglycol dimethyl ether, and admixing the solution with tert-butyl dimethylether to form a suspension comprising of the said crystalline form.

The solution of Imatinib mesylate in ethyleneglycol dimethyl ether is provided by heating a combination of imatinib base and ethyleneglycol dimethyl ether to obtain a solution, and admixing the solution with methanesulfonic acid. Preferably, the heating is to a temperature of about 0° C. to about 70° C., more preferably to about 25° C. to about 60° C., even more preferably to about 40° C. The solution is then cooled, prior to the addition of tert-butyl dimethylether. Preferably, cooling is to a temperature of about 20° C. to about 0° C., more preferably, to about 10° C.

As one skilled in the art will appreciate, the time required to obtain Form α imatinib mesylate will vary depending upon, among other factors, the amount of precipitate to be cooled and the cooling temperature, and can be determined by taking periodic XRD readings. Recovery of imatinib mesylate Form α is performed by any means known in the art such as by filtering, washing and drying. Preferably, the drying is at a temperature of about 60° C. to about 80° C., more preferably in a vacuum.

The present invention encompasses a process for preparing crystalline imatinib mesylate Form α by slurrying imatinib mesylate selected from a group consisting of: forms IX, VIII and mixtures thereof, in a solvent selected from the group consisting of: ethylacetate, acetone, and mixtures thereof.

Usually, the slurry is maintained at a temperature of about −5° C. to about 20° C., preferably at a temperature of about 0° C. to about 5° C., more preferably at a temperature of about 0° C., to allow the transition of the starting crystalline form to form α. Preferably, the slurry is maintained at such temperature for a period of about 4 hours to about 24 hours, more preferably for a period of about 10 hours to about 18 hours, more preferably, about 12 hours.

As one skilled in the art will appreciate, the time required to obtain Form α imatinib mesylate will vary depending upon, among other factors, the amount of precipitate to be cooled and the cooling temperature, and can be determined by taking periodic XRD readings. Recovery of imatinib mesylate Form α is performed by any means known in the art such as by filtering, washing and drying. Preferably, drying is at a temperature of about 60° C. to about 80° C., more preferably in a vacuum.

The present invention further encompasses a process for preparing the amorphous form of imatinib mesylate by a process comprising: providing a solution of imatinib mesylate in a solvent selected from the group consisting of: methanol, methoxyethanol or ethoxyethanol, N-methylpyrrolidone, propylene carbonate, acetonitrile, nitromethane, pyridine, dimethylsulfoxide, or a mixture thereof; and admixing with an anti-solvent selected from the group consisting of: ethylacetate butylacetate, diethyl ether, tert-butyl methyl ether, tetrahydrofuran, dioxane, methylal, ethylal and 1,3-dioxolane to obtain a precipitate.

The solution is prepared by dissolving imatinib mesylate in the solvent at a temperature of about 20° C. to about 100° C., preferably at about 0° C. to about 80° C., more preferably at about 20° C. to about 60° C.

Alternatively, the solution may be prepared by admixing imatinib base, methanesulfonic acid and a solvent selected from the group consisting of: methanol, methoxyethanol or ethoxyethanol, N-methylpyrrolidone, propylene carbonate, acetonitrile, nitromethane to obtain a mixture; and heating the mixture to obtain an imatinib mesylate solution. Heating the mixture to obtain an imatinib mesylate solution is preferably to a temperature of about 20° C. to about 85° C., more preferably of about 60° C. to about 80° C. Preferably, the obtained solution is further cooled to a temperature of about 20° C. to about 0° C. prior to the addition of the anti-solvent. Preferably the solution of imatinib mesylate is gradually added to the anti-solvent under stirring. Preferably, the solution of imatinib mesylate is added to an excess of anti-solvent.

Figure 30:
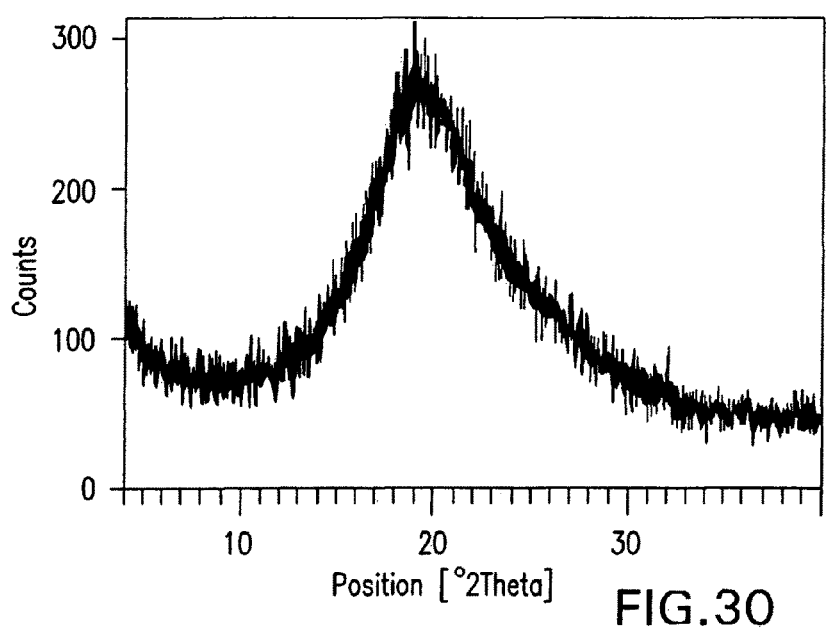
FIG. 30 illustrates a powder X-ray diffraction pattern for amorphous imatinib mesylate.
Figure 31:
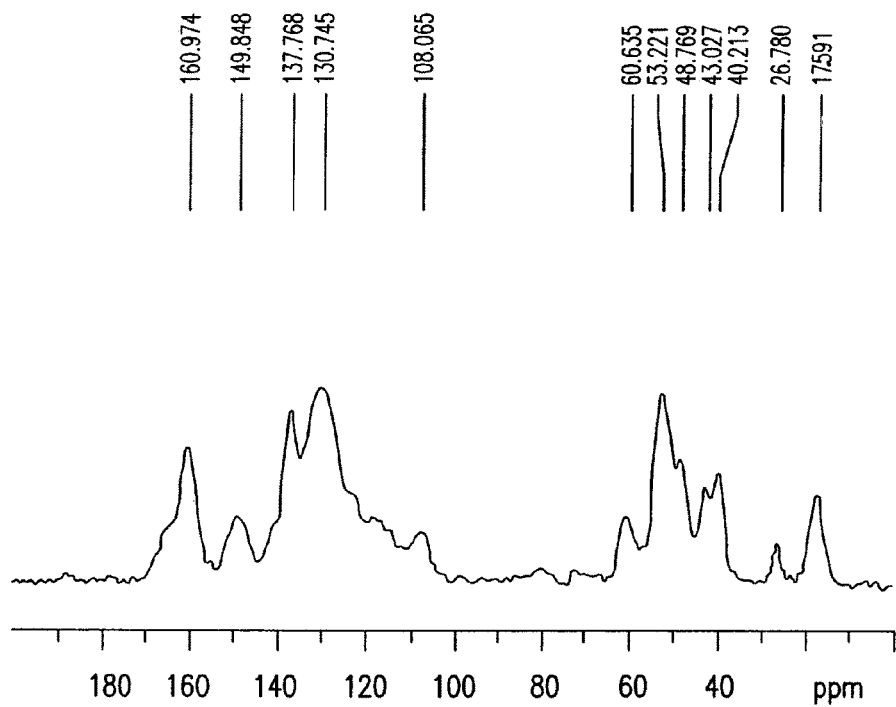
FIG. 31 illustrates a solid-state $^{13}$C NMR spectrum of amorphous imatinib mesylate.

The process may further comprise a recovery process. Recovery of the amorphous imatinib mesylate is preformed by any means known in the art such as by filtering, washing and drying. The amorphous form according to the invention may be substantially identified by the PXRD pattern and $^{13}C$ NMR spectrum depicted in FIGS. 30 and 31, respectively.

The present invention further encompasses a process for preparing amorphous imatinib mesylate comprising: providing a solution of imatinib mesylate in solvent selected from a group consisting of: isobutanol, n-butanol, methoxyethanol or ethoxyethanol, N-methylpyrrolidone, acetic acid, propylene carbonate, acetonitrile, nitromethane, pyridine, dimethylsulfoxide, and mixture thereof; and cooling the solution to a temperature of about 30° C. to about −50° C., preferably to a temperature of about 0° C. to about −50° C., more preferably to about −30° C. to about −50° C., to obtain the amorphous imatinib mesylate.

The solution is preferably prepared by dissolving imatinib mesylate at an elevated temperature depending on the solvent used. Preferably, the solvent is either n-butanol or isobutanol. Preferably, the elevated temperature is of about 40° C. to the boiling point of the solvent. Preferably, the cooling is carried out gradually. Preferably, the gradually cooling comprises cooling the solution to a temperature of about 0° C. to about −20° C., and further cooling to a temperature of about −30° C. to about −50° C. As one skilled in the art will appreciate, the time required to obtain amorphous imatinib mesylate will vary depending upon, among other factors, the amount of precipitate to be cooled and the cooling temperature, and can be determined by taking periodic XRD readings, preferably the time period for cooling the solution is from about 4 hours to about 24 hours, more preferably from about 14 hours to about 18 hours. Recovery of the crystalline imatinib mesylate is preformed by any means known in the art such as by filtering, washing and drying.

The present invention comprises a pharmaceutical composition comprising any one of imatinib mesylate forms of the present invention and at least one pharmaceutically acceptable excipient.

The present invention comprises a pharmaceutical composition comprising imatinib mesylate of any one of imatinib mesylate forms made by the processes of the present invention, and at least one pharmaceutically acceptable excipient.

The present invention further encompasses a process for preparing a pharmaceutical formulation comprising combining any one of imatinib mesylate forms of the present invention with at least one pharmaceutically acceptable excipient.

The present invention further encompasses a process for preparing a pharmaceutical formulation comprising combining any one of imatinib mesylate forms made by the processes of the present invention, and at least one pharmaceutically acceptable excipient.

The present invention further encompasses the use of any one of imatinib mesylate forms of the present invention for the manufacture of a pharmaceutical composition.

The present invention further encompasses the use of any one of imatinib mesylate forms made by the processes of the invention, for the manufacture of a pharmaceutical composition.

Methods of administration of a pharmaceutical composition of the present invention may comprise administration in various preparations depending on the age, sex, and symptoms of the patient. The pharmaceutical compositions can be administered, for example, as tablets, pills, powders, liquids, suspensions, emulsions, granules, capsules, suppositories, injection preparations (solutions and suspensions), and the like. When the pharmaceutical composition comprises any one of the above crystalline imatinib mesylate Forms the liquid pharmaceutical composition is a suspension or emulsion, wherein imatinib mesylate retains its crystalline form.

Pharmaceutical compositions of the present invention can optionally be mixed with other forms of imatinib mesylate and/or other active ingredients. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, and the like.

Diluents increase the bulk of a solid pharmaceutical composition and can make a pharmaceutical dosage form containing the composition easier for the patient and care giver to handle. Diluents for solid compositions include, for example, microcrystalline cellulose (e.g., Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, or talc.

Carriers for use in the pharmaceutical compositions may include, but are not limited to, lactose, white sugar, sodium chloride, glucose, urea, starch, calcium carbonate, kaolin, crystalline cellulose, or silicic acid.

Binders help bind the active ingredient and other excipients together after compression. Binders for solid pharmaceutical compositions include for example acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, or starch.

Disintegrants can increase dissolution. Disintegrants include, for example, alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Disintegration inhibitors may include, but are not limited to, white sugar, stearin, coconut butter, hydrogenated oils, and the like.

Absorption accelerators may include, but are not limited to, quaternary ammonium base, sodium laurylsulfate, and the like.

Wetting agents may include, but are not limited to, glycerin, starch, and the like. Adsorbing agents may include, but are not limited to, starch, lactose, kaolin, bentonite, colloidal silicic acid, and the like.

A lubricant can be added to the composition to reduce adhesion and ease release of the product from a punch or dye during tableting. Lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Glidants can be added to improve the flowability of non-compacted solid composition and improve the accuracy of dosing. Excipients that can function as glidants include for example colloidal silicon dioxide, magnesium trisilicate, powdered cellulose, starch, talc and tribasic calcium phosphate.

Flavoring agents and flavor enhancers make the dosage form more palatable to the patient. Common flavoring agents and flavor enhancers for pharmaceutical products that can be included in the composition of the present invention include for example maltol, vanillin, ethyl vanillin, menthol, citric acid, fumaric acid, ethyl maltol, and tartaric acid.

Tablets can be further coated with commonly known coating materials such as sugar coated tablets, gelatin film coated tablets, tablets coated with enteric coatings, tablets coated with films, double layered tablets, and multi-layered tablets. Capsules can be coated with shell made, for example, from gelatin and optionally contain a plasticizer such as glycerin and sorbitol, and an opacifying agent or colorant.

Solid and liquid compositions can also be dyed using any pharmaceutically acceptable colorant to improve their appearance and/or facilitate patient identification of the product and unit dosage level.

In liquid pharmaceutical compositions of the present invention, the imatinib mesylate of the present invention is suspended together with any other solid ingredients, which may be dissolved or suspended, in a liquid carrier, such as water, vegetable oil, alcohol, polyethylene glycol, propylene glycol or glycerin. In suspension the Imatinib mesylate retains its crystalline form.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain viscosity enhancing agents to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at safe levels to improve storage stability.

A liquid pharmaceutical composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by an experienced formulation scientist in view of standard procedures and reference works known in the art.

A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

When shaping the pharmaceutical composition into pill form, any commonly known excipient used in the art can be used. For example, carriers include, but are not limited to, lactose, starch, coconut butter, hardened vegetable oils, kaolin, talc, and the like. Binders used include, but are not limited to, gum arabic powder, tragacanth gum powder, gelatin, ethanol, and the like. Disintegrating agents used include, but are not limited to, agar, laminalia, and the like.

For the purpose of shaping the pharmaceutical composition in the form of suppositories, any commonly known excipient used in the art can be used. For example, excipients include, but are not limited to, polyethylene glycols, coconut butter, higher alcohols, esters of higher alcohols, gelatin, semisynthesized glycerides, and the like.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added. If necessary, coloring agents, preservatives, perfumes, seasoning agents, sweetening agents, and other medicines may also be added to the desired preparations during the treatment of schizophrenia.

The amount of imatinib mesylate of the present invention contained in a pharmaceutical composition according to the present invention is not specifically restricted; however, the dose should be sufficient to treat, ameliorate, or reduce the condition.

Having described the invention with reference to certain preferred embodiments, other embodiments will become apparent to one skilled in the art from consideration of the specification. The disclosures of the references referred to in this patent application are incorporated herein by reference. The invention is further defined by reference to the following examples describing in detail the process and compositions of the invention. It will be apparent to those skilled in the art that many modifications, both to materials and methods, may be practiced without departing from the scope of the invention.

EXAMPLES

Instruments

XRD

XRD diffraction was performed on X-Ray powder diffractometer: Philips X'pert Pro powder diffractometer, Cu-tube, scanning parameters: CuK$_\alpha$ radiation, $\lambda$=1.5418 Å. Continuous scan at a rate of: 0.02° 2theta/0.3 sec.

$^{13}$C NMR

The CP/MAS $^{13}$C NMR measurements were made at Bruker Avance 500 NMR US/WB spectrometer in 4-mm ZrO$_2$ rotor. Magic angle spinning (MAS) speed was 10 kHz. As used herein, the term "$^{13}$C NMR chemical shifts" refers to the shifts measured under above specified conditions, however, these shifts can slightly differ instrument to instrument and can be shifted either upfield or downfield due to the different instrumental setup and calibration used. Nevertheless the sequence of individual peaks remains identical.

Water Content

Water content was determined by Karl Fischer titrator TIT-RANDO 841, software Tiamo 1.1 (Metrohm). Solution used for determination: Hydranal Composite 2 (Riedel de Haen). Sampling: 100.00 mg, 2 repeats.

Residual Solvents Determination—Gas Chromatography

Residual solvents were determined by gas chromatography using head-space sampling. Headspace instrument Tecmar HT3 together with Gas chromatograph A6890 equipped with FID detector (Agilent technologies). Sample amount 100 mg with 1 ml of N,N-dimenthylformamid is mixed in 20-ml headspace vial, after equilibration (30 min.) in the headspace oven (80° C.) 1 ml of vapour phase is injected into GC. GC column: Equity-5: 30 m×0.53 mm ID×5 µm (5%—Phenylmethylpolysiloxane); Injector temperature: 200° C., split 1:4; FID detector temperature: 250° C.; GC oven: 40° C. (10 min.)—10° C./min. to 120° C. (0 min.)—40° C./min. to 220° C. (2 min.), He: 23 kPa (40° C.), 33 cm/sec., constant flow.

NMR Spectroscopy in Solution

NMR spectra of solutions in deuterated dimethylsulfoxide were measure on Varian INOVA-400 spectrometer using 399.87 MHz for 1H and 100.55 MHz for 13 C at 30° C.

Example 1

Preparation of Imatinib Mesylate Form IV

Imatinib base (3 g) was suspended in ethanol (60 ml, 96%) at −10° C. Methanesulfonic acid (0.375 ml) was added with stirring and the suspension was stirred for additional 20 min at −5° C. obtaining thus the solution of imatinib mesylate. Than the solution was allowed to crystallize without stirring at −5° C. for 3 hours. t-Butyl methyl ether (50 ml) was added, the white solid was filtered, washed with petrolether (50 ml) and dried in a stream of nitrogen for 1 h to obtain imatinib mesylate Form IV (3.18 g, yield: 89%).

Example 2

Preparation of Imatinib Mesylate Form IV

Imatinib mesylate Form α (3 g) was suspended in ethanol (40 ml) and the suspension was heated at 50° C. Than water was added (roughly 1 ml) till the dissolution of imatinib mesylate. The solution thus formed was allowed to crystallise at 0° C. overnight. t-Butyl methyl ether (50 ml) was added, the white solid was filtered, washed with petrolether (50 ml) and dried in a stream of nitrogen for 1 h to obtain imatinib mesylate Form IV (2.70 g, yield: 90%).

Example 3

Preparation of Imatinib Mesylate Form IV

Imatinib base (3 g, 0.0061 mole) was suspended in dry ethanol (60 ml). The suspension was cooled to −40° C. and then an ethanol-solution of methanesulfonic acid (0.591 g in 3.59 ml; 0.0061 mole) was added at once. Exactly after 5 min of stirring at −40° C. the seeding crystal (Form IV, 0.1 g) was put into the suspension. The stirring was maintained for additional 25 minutes in the temperature range from −40° C. to −35° C. Then the suspension was let to stay in freezer at −28° C. for 14 hours. In the course of standing, the major part of crystalline phase was created—important requirement is absence of motion. After standing the suspension was diluted with MTBE (50 ml) and crystalline product was filtered. The cake was rinsed with MTBE (20 ml) and dried by flow of nitrogen through the filter for 2 hrs (product is moisture sensitive). Imatinib mesylate (Form IV) was obtained (3.61 g; yield: 90.1%).

Example 4

Preparation of Imatinib Mesylate Form V

Imatinib base (1 g) was suspended in 1,3-dioxolane (4.5 ml) at 15° C. Aqueous methanesulfonic acid (0.125 ml in 0.5 ml of water) was added obtaining the solution of imatinib mesylate. The solution thus formed was cool down to about 10° C. and additional portion of 1,3-dioxolane (15 ml) was added into the mixture. The suspension was stirred at 5° C. for 3 h, providing form VI. The white solid was filtered, washed with 1,3-dioxolane, and the solid matter was dried first for 6 h at RT and than for 6 h at 60° C. under flow of nitrogen to obtain imatinib mesylate Form V (1.0 g, yield: 84%).

Example 5

Preparation of Imatinib Mesylate Form V

The dioxolane solvate Form VI (81 g) was ground, placed into laboratory oven and heated in temperature range from 65° to 70° C. under gentle stream of nitrogen (150 l/hr). The desolvation was monitored by DSC (the peak of the solvate at 90° C. was disappearing) and GC. The 1,3-dioxolane content (according to GC) at the end dropped under 890 ppm. The drying time was about 8 hrs. Imatinib mesylate (Form V; anhydrate) was obtained (72 g; yield: 100%).

Example 6

Preparation of Imatinib Mesylate Form V

Imatinib mesylate Form VI was dried on the filter under vacuum for 18 hours. Than the product was dried in the oven at 60° C. under vacuum until the dioxolane amount of 890 ppm by GCL analysis was obtained.

Example 7

Preparation of Imatinib Mesylate Form VI

Imatinib base (1 g) was suspended in aqueous 1,3-dioxolane (5 ml, 10% of water, v/v) at 15° C. Methanesulfonic acid (0.125 ml) was added obtaining the solution of imatinib mesylate. The solution thus formed was cool down to about 10° C. and additional portion of 1,3-dioxolane (15 ml) was added into the mixture. The suspension was stirred at 5° C. for 10 min and the white solid was filtered, washed with 1,3-dioxolane, and the solid matter was dried at 25° C. under N$_2$ flow for 4 h to obtain imatinib mesylate Form VI (0.6 g, yield: 50%).

Example 8

Preparation of Imatinib Mesylate Form VI

Imatinib base (75 g, 0.152 mole) was placed into double-jacketed glass-reactor and suspended with water-1,3-dioxolane mixture (37.5 ml: 712.5 ml). The content of the reactor was kept (for all the time) under gentle nitrogen stream. The temperature was adjusted at 20° C., undiluted methanesulphonic acid (14.21 g, 0.148 mole) was added (at once or dropwise during a few minutes). The two-phase liquid was stirred cca 50 min at 20° C. Then temperature inside the reactor was adjusted at +10° C. and the solution was kept at that temperature 1 hr. In the course of stirring a dense crystalline suspension was formed. The temperature was lowered at +5° C. and stirring was proceeding for the next 4 hrs. At the end the suspension was diluted with an additional amount of dry dioxolane (750 ml) and let to stay overnight in a fridge at approximately +5° C. Then the crystalline phase was filtrated off and rinsed with dioxolane (150 ml). The filtration cake was powdered and dried by blowing gentle stream of nitrogen through the cake (solid phase is very hydroscopic). The drying process was monitored by measuring LOD (loss on drying)—it was finished when LOD reached 11-12%.

Imatinib mesylate (Form VI; 1,3-dioxolane-solvate) was obtained (81 g; yield: 80.5%).

Example 9

Preparation of Imatinib Mesylate Form VI

Imatinib base (600 g), 5.7 liters of 1,3-dioxolane and 300 ml of water were added to a vessel. The suspension was stirred at 20° C. for 15 minutes and than 113.3 g of methanesulphonic acid was added. After addition the solution was cooled from 20° C.-10° C. in 1 hour and after 1 hour of stirring the solution was cooled again from 10° C.-5° C. in 1 hour. The suspension was stirred for 4 hours at 5° C. Than 6 liters of dioxolane was added in 30 minutes maintaining the temperature at 5° C. The suspension was left for 2.5 hours at 5° C. without stirring. The suspension was filtered and the product was washed with 6 liters of 1,3-dioxolane.

Example 10

Preparation of Imatinib Mesylate Form VI

Imatinib mesylate (8 g, 0.0136 mole) was poured into a beaker with the water-1,3-dioxolane mixture (5 ml+45 ml). The salt was dissolved to limpid solution by heating up to 65° C. Another volume of 1,3-dioxolane (50 ml) was placed into a round-bottom flask in a freezing bath and cooled to −5° C. The hot solution of imatinib mesylate was dosed into chilled 1,3-dioxolane in such a way that the temperature did not exceeded +20° C. After that the temperature of solution in the flask was adjusted at +5° C. and the content was stirred for 3 hrs. In the course of stirring the crystalline form VI created. Then the dense suspension was diluted with dry 1,3-dioxolane (100 ml), the crystalline solid was filtrated off and rinsed with 1,3-dioxolane (20 ml). Free solvent was removed by drying on the filter—under nitrogen stream at room temperature (solid phase is very hydroscopic).

Imatinib mesylate (Form VI; 1,3-dioxolane-solvate) was obtained (6.53 g; yield: 81.6%).

Example 11

Preparation of Imatinib Mesylate Form VII

Imatinib base (1 g) was dissolved in nitromethane (20 ml) at 90° C. and methanesulfonic acid (0.125 ml) was added. The solution thus formed was allowed to crystallise at 10° C. for 5 h. The white solid was filtered, washed with t-butyl methyl ether, and the solid matter was dried in a stream of nitrogen for 4 h to obtain imatinib mesylate Form VII (1.1 g, yield: 93%).

Example 12

Preparation of Imatinib Mesylate Form VIII

Imatinib base (1 g) was suspended in a mixture of isopropanol and water (30 ml, 95:5 V/V) at −10° C. Methanesulfonic acid (0.125 ml) was added with stirring and the suspension was stirred for additional 20 min at −5° C. obtaining thus the solution of imatinib mesylate. Then the solution was allowed to crystallize without stirring at −15° C. for overnight. t-Butyl methyl ether (30 ml) was added, the white solid was filtered, washed with petrolether (50 ml) and dried in a stream of nitrogen for 1 h to obtain imatinib mesylate Form VIII (1.0 g, yield: 85%).

Example 13

Preparation of Imatinib Mesylate Form VIII

Imatinib base (20 g; 0.0405 mole) was suspended in isopropanol (723 ml) and water (24.1 ml) was added. The suspension was cooled to −10° C. Then an isopropanolic-solution of methanesulphonic acid (3.7 g in 19.3 ml of isopropanol; 0.385 mole) was added dropwise into suspension during about 10 minutes. When dosing of methanesulphonic acid was finished the temperature was adjusted at −1° C. and the suspension was stirred about 1 hour and the mixture was placed overnight in a freezer at −28° C. Then, the crystalline product was filtered. The cake was rinsed with MTBE (20 ml) and dried by blowing nitrogen through the filter for 2 hours). Imatinib mesylate Form VIII was obtained (22.90 g; yield: 88.2%).

Example 14

Preparation of Imatinib Mesylate Form IX

Imatinib mesylate Form IV (530 mg) was suspended in t-butyl methyl ether (20 ml) and stirred at 20° C. for 20 h. The white solid was filtered, washed with t-butyl methyl ether, and the solid matter was dried at 60° C. in vacuum for 2 h to obtain imatinib mesylate Form IX (595 mg, yield: 93%).

Example 15

Preparation of Imatinib Mesylate Form IX

Imatinib base (20 g) was suspended in tetrahydrofuran (350 ml) at 10° C. Traces of peroxides were removed from tetrahydrofuran by filtration through basic alumina prior to use. Methanesulfonic acid (2.5 ml in 50 ml of cooled tetrahydrofuran) was added with vigorous stirring within 20 minutes. The suspension was stirred for additional 20 min. The temperature was kept not to exceed 20 C. The white solid was filtered, washed with tetrahydrofuran, and the solid matter was dried at 90° C. in vacuum for 2 h to obtain imatinib mesylate Form IX (18.2 g, yield: 76%).

Example 16

Preparation of Imatinib Mesylate Form IX

Imatinib mesylate Form V (1 g) was suspended in t-butyl methyl ether (20 ml) and stirred at 20° C. for 20 h. The white solid was filtered, washed with t-butyl methyl ether, and the solid matter was dried at 60° C. in vacuum for 2 h to obtain imatinib mesylate Form IX (1 g, yield: 100%).

Example 17

Preparation of Imatinib Mesylate Form X

Imatinib mesylate Form IV (1 g) was placed on a Buchner funnel termostated at 0-5° C. Nitrogen stream was applied for drying of imatinib mesylate Form IV at 0-5° C. for 8 h and than the temperature was increased to 25° C. and nitrogen stream was applied for additional 10 h to obtain imatinib mesylate Form X.

Example 18

Preparation of Imatinib Mesylate Form X

Imatinib base (60 g; 0.1216 mole) was suspended in 1200 ml of Ethanol and stirred. Reactor was kept under flow of nitrogen during all of the experiment (6 litres per hour). Then, 24 ml of water was added to the suspension and the temperature was adjusted at –15° C. An ethanolic solution of methanesulfonic acid (79.8 ml 10% V/V; 0.1213 mole) was added during 2 minutes to the reaction mixture. Temperature of the solution was set at –10° C. during 10 minutes, imatinib base was dissolved and seeding material of form X (2 g) was added. The crystallization process was continued under stirring for 190 minutes and temperature was continuously increased to –5° C. The suspension was stored overnight in a freezer at approx. –27° C. Than, suspension was diluted by 1000 ml TBME, filtered by nitrogen pressure and obtained crystalline portion was washed with 400 ml TBME. The resulted crystalline form X was dried by flow of nitrogen through the filter to remove free ethanol. Ethanol content was about 7.5%. (Yield was 67.95 g; 85%)

Example 19

Preparation of Imatinib Mesylate Form X

Imatinib base (12 g, 0.0243 mole) was suspended in 240 ml of ethanol and 4.8 ml of water was added under stirring. Reactor was kept under flow of nitrogen during all of the experiment (6 litres per hour). Temperature of the mixture was adjusted at –15° C. and an ethanolic solution of methanesulphonic acid (15.9 ml of 10% V/V; 0.0241 mole) was added at once into the suspension. The base was slowly dissolved and a new solid phase of imatinib mesylate started to crystallize during 15 minutes. The suspension was stirred for 3 hours and temperature was maintained in range from –10° C. to –5° C. Then the suspension was let to stay overnight in a freezer at approx. –27° C.

After that, the suspension is diluted by 200 ml TBME and after 10 minutes of stirring the crystalline phase was filtered by nitrogen pressure and the obtained crystalline portion was washed by 80 ml TBME. The resulted crystalline form X was dried by flow of nitrogen through the filter to remove free ethanol. Ethanol content was about 7.5%.

Example 20

Preparation of Partially Dried Imatinib Mesylate Form X

Imatinib mesylate Form X obtained form previous examples is dried in a laboratory oven under nitrogen flow at 80° C. Flow of nitrogen was adjusted at 150 litres per hour. Alternatively, Form X could be dried in rotary evaporator equipped with drying-flask under atmospheric pressure flow of nitrogen (150 liters per hour). Bath temperature was adjusted at 80° C. Drying process was monitored by GC and final ethanol content was typically about 6% or less.

Example 21

Preparation of Imatinib Mesylate Form X

Imatinib base (1926 g) was suspended in 38.5 liters of ethanol and 2 liters of water was added under stirring. Reactor was kept under flow of nitrogen during all of the experiment. Temperature of the mixture was adjusted at –15° C. and an ethanolic solution of methanesulphonic acid (375 g of methanesolphonic acid in 2278 ml of Ethanol) was added into the suspension. The temperature was increased to about –13° C. In 15 minutes, the product partially dissolved and recrystallized. After 15 minutes the seeding material of Form X (20 g suspended in chilled ethanol) was added. The temperature was slightly increased up to –5° C. in 3 hours and than 32 liters of TBME was added dropwise in 45 minutes. The mixture was stirred for 30 minutes and then filtered and washed with an additional 5 liters of TBME. The resulted crystalline form X was dried on filter by flow of nitrogen through the filter to remove free ethanol. Ethanol content was about 7.5%.

Example 22

Preparation of Partially Dried Imatinib Mesylate Form X

Imatinib mesylate Form X, obtained according to example 21, was dried on filter drier heated up to 90° C. under flow of nitrogen. Drying procedure was performed to obtaining residual ethanol content around 4% (Yield 2276 g). The drying process was monitored by .GC.

Example 23

Preparation of Partially Dried Imatinib Mesylate Form X

Imatinib base (60 g, 0.1216 mol) was suspended in EtOH (900-1200 mL) and water (2-5% v/v vs EtOH) was added under stirring. The temperature was adjusted to –10/–5° C. and a solution of MeSO3H in EtOH (79.8 mL 10% v/v; 0.1213 mol) was added in 2 min, keeping the temperature at –10/–5° C.

The reaction mixture was seeded with Imatinib mesylate form X (300-500 mg) and kept under stirring at –5° C. for 3 h. The suspension was diluted with MTBE (750-1000 mL) keeping the temperature below 0° C. The solid was filtered off, washed with MTBE and dried under vacuum onto the filter in a nitrogen atmosphere to remove free EtOH. Crystalline Imatinib mesylate form X containing about 7% EtOH was obtained in 92-95% yield.

Example 24

Procedure for Preparation of Partially Dried Imatinib Mesylate FormX

Imatinib mesylate prepared according to one of the above described procedure was dried by flowing hot nitrogen at a temperature between 30° C. and 90° C., obtaining pure FormX (solvation EtOH 7.3%; MTBE<100 ppm; Py<200 ppm). EtOH content was further reduced by slowly heating up the product under intermittent stirring from 30° C. to 90° C. in a time range of 12-24 h, under a continuous pre-heated nitrogen flow.

Example 25

Preparation of Imatinib Mesylate Form X

Imatinib mesylate Form V (500 mg) was suspended in 0.5 ml of ethanol and mixed for 10 minutes at 25° C. The substance crystallized to solid form and was dried under nitrogen sweep for 1 hour at 60° C. PXRD analysis of the crystal before and after drying revealed form X.

Example 26

Preparation of Imatinib Mesylate Form XI

Imatinib base (20 g) was suspended in tetrahydrofuran (350 ml) at 10° C. Traces of peroxides were removed from tetrahydrofuran by filtration through basic alumina prior to use. Methanesulfonic acid (2.5 ml in 50 ml of cooled tetrahydrofuran) was added with vigorous stirring within 20 minutes. The suspension was stirred for additional 20 min. The temperature was kept not to exceed 20° C. Then the temperature was decreased to 10° C. again. The white solid was filtered, washed with tetrahydrofuran, and recovered without further drying to obtain imatinib mesylate Form XI.

Example 27

Preparation of a Composition of Amorphous and Form IV of Imatinib Mesylate

Imatinib mesylate Form IV (1 g) according to the Example 1 was suspended in n-heptane (40 ml). The suspension was heated to 98° C. for 15 min. The white solid was filtered and the solid matter was dried at 60° C. in vacuum for 2 h to obtain imatinib mesylate Form XII (0.9 g, yield: 97%).

Example 28

Preparation of Imatinib Mesylate Form XIII

Imatinib mesylate Form IV (1 g) according to the Example 1 was placed in an thermostated oven in a stream of nitrogen (150 l/h), and dried at 60° C. for 20 h to obtain imatinib mesylate Form XIII (0.9 g, yield: 97%).

Example 29

Preparation of a Composition of Amorphous and Form IV of Imatinib Mesylate

Imatinib mesylate Form IV (2 g) was placed on a Petri-dish into a laboratory oven and heated at 80° C. for 2 hrs under gentle nitrogen stream was obtained Imatinib mesylate Form XII (1.84 g; yield: 92%).

Example 30

Preparation of Imatinib Mesylate Form XIV

Imatinib base (4 g) was suspended in isopropanol (80 ml) and water (11 ml) at −10° C. Methanesulfonic acid (0.5 ml in 4 ml of isopropanol) was added with stirring and the suspension was stirred for additional 20 min at −5° C. obtaining thus the solution of imatinib mesylate. Then the solution was allowed to crystallize without stirring at −20° C. overnight. The white solid was filtered at −10° C., washed with isopropanol (10 ml) and dried in a stream of nitrogen for 1 h to obtain imatinib mesylate Form XIV (3 g).

Example 31

Preparation of Imatinib Mesylate Form XV

Imatinib mesylate (1.6 g) was dissolved in acetic acid (8 ml). Butylacetate (78 ml) was added to the solution with stirring facilitating thus the crystallisation of imatinib mesylate Form XV. Than the suspension of imatinib mesylate Form XV was allowed to crystallize without stirring at 0° C. overnight. The crystals of imatinib mesylate Form XV were filtered, washed with t-butyl methyl ether (20 ml), petrolether (20 ml), and dried in a stream of nitrogen for 1 h at 25° C. to obtain imatinib mesylate Form XV (1.2 g, yield: 68%). Sample was examined by solution and solid-state NMR providing the imatinib:acetic acid ratio roughly 1:1.

Example 32

Preparation of Imatinib Mesylate Form XVI

Imatinib mesylate Form XV (250 mg) was heated at vacuum oven at 5 mBar and 60° C. for 1 h to obtain imatinib mesylate Form XVI (230 mg, yield: 97%). Sample was examined by solution NMR providing the imatinib:acetic acid ratio roughly 1:1/2.

Example 33

Preparation of Imatinib Mesylate Form α

Amorphous imatinib mesylate (1 g) was dissolved in 1,2-propylene carbonate (8 ml) at 70° C. The solution thus formed was allowed to crystallise at 20° C. overnight. The white solid was filtered, washed with t-butyl methyl ether, and the solid matter was dried at 60° C. in vacuum for 2 h to obtain imatinib mesylate Form α (0.94 g, yield: 94%).

Example 34

Preparation of Imatinib Mesylate Form α

Imatinib mesylate Form VI (3.67 g) was added to the solution containing n-propanol (150 ml) and acetic acid 370 µl).

The suspension was heated to 60° C. providing a clear solution. The volume of solution was reduced to 35 ml by evaporation at the vacuum evaporator at 20 mBar and the resulting solution was allowed to crystallize overnight at 15° C. Imatinib mesylate Form α was recovered by filtration and dried by a stream of nitrogen. Yield 3.01 g (92%).

Example 35

Preparation of Imatinib Mesylate Form α

Imatinib base (3 g) was added to the solution of n-propanol (30 ml) and acetic acid (0.5 ml). The suspension was heated under reflux (82° C.) for 15 min providing thus a clear solution of imatinib acetate. Methanesulfonic acid (375 μl) was added providing the replacement of week acetic acid by stronger methanesulfonic acid and the volume of solution was reduced to ½ by evaporation at the vacuum evaporator at 20 mBar. Seeds of imatinib mesylate Form α were added (20 mg) and the solution was allowed to crystallize overnight. Crystals of imatinib mesylate Form a were recovered by filtration, washed with n-propanol, n-hexane and dried at 80° C. in a stream of nitrogen. Yield 2.97 g (83%).

Example 36

Preparation of Imatinib Mesylate Form α

Imatinib base (0.5 g) was dissolved in ethyleneglycoldimethylether (4 ml) at 40° C. and methanesulfonic acid was added (63 μl). The solution was cooled to 10° C. and tert-butyl dimethyl ether was added with stirring. Imatinib mesylate Form α was recovered by filtration, washed with tert-butyl dimethyl ether and dried at 80° C. in a stream of nitrogen. Yield 570 mg (95%).

Example 37

Preparation of Imatinib Mesylate Form α

Imatinib mesylate form IX (500 mg) was suspended in ethylacetate (10 ml) and the suspension was stirred overnight at 0° C. Imatinib mesylate Form α was recovered by filtration, washed with ethylacetate and dried at 80° C. in a stream of nitrogen. Yield 480 mg (96%).

Example 38

Preparation of Imatinib Mesylate Form α

Imatinib mesylate form IX (500 mg) was suspended in acetone (10 ml) and the suspension was stirred overnight at 0° C. Imatinib mesylate Form α was recovered by filtration, washed with ethylacetate and dried at 80° C. in a stream of nitrogen. Yield 470 mg (94%).

Example 39

Preparation of Imatinib Mesylate Form α

Imatinib mesylate Form VIII (500 mg) was added to acetone (10 ml) and the suspension was stirred overnight at 0° C. Imatinib mesylate Form α was recovered by filtration, washed with ethylacetate and dried at 80° C. in a stream of nitrogen. Yield 430 mg (95%).

Example 40

Preparation of Amorphous Imatinib Mesylate from Iso-Butanol

Imatinib mesylate (2.5 g) was dissolved in iso-butanol (120 ml) under heating. The solution was allowed to cool to the ambient temperature (20° C.) and then cooled at −30° C. for 15 h. Then the precipitated amorphous imatinib mesylate was washed subsequently with small amount of tert-butyl methyl ether and petrolether and dried to give 1.9 g of amorphous imatinib mesylate.

Example 41

Preparation of Amorphous Imatinib Mesylate

Imatinib mesylate (2 g) was dissolved in n-butanol (50 ml) under heating. The solution was allowed to cool to the ambient temperature (20° C.) and than cooled at −50° C. for 15 h. Then the precipitated amorphous imatinib mesylate was washed subsequently with small amount of tert-butyl methyl ether and petrolether and dried to give 1.5 g of amorphous imatinib mesylate.

Example 42

Preparation of Amorphous Imatinib Mesylate from Methanol/Diethyl Ether

Imatinib mesylate (3 g) was dissolved in methanol (15 ml) under heating. The solution was allowed to cool to the ambient temperature (20° C.) and than was added to the stirred diethyl ether (300 ml). Then the precipitated amorphous imatinib mesylate was filtered, washed with small amount of petrolethether and dried to give 2.8 g of amorphous imatinib mesylate.

Example 43

Preparation of Amorphous Imatinib Mesylate from Methanol/Tert-Butyl Methyl Ether Imatinib mesylate (1 g) was dissolved in methanol (5 ml) under heating. The solution was allowed to cool to the ambient temperature (20° C.) and than was added to the stirred tert-butyl methyl ether (80 ml). Then the precipitated amorphous imatinib mesylate was filtered, washed with small amount of petrolether and dried to give 0.8 g of amorphous imatinib mesylate.

Example 44

Preparation of Imatinib Base

A solution of 8.0 g (28.85 mmol) of N-(5-amino-2-methylphenyl)-4-(3-pyridyl)-2-pyrimidine-amine and 10.68 g (32.8 mmol) of 4-(4-methyl-piperazinomethyl)-benzoyl chloride in 320 ml of pyridine are stirred under nitrogen at room temperature for 23 hours. The reaction mixture is concentrated under HV; 200 ml of water are added and, after cooling to 0° C., the mixture is filtered. After drying at 80° C. under HV, the crude product is made into a slurry with $CH_2Cl_2$/methanol (95:5) and filtered, yielding N-{5-[4-(4-methyl-piperazinomethyl)-benzoylamido]-2-methylphenyl}-4-(3-pyridyl)-2-pyrimidine-amine. After separation by chromatography there are obtained further amounts of that product; m.p. 211° C.-213° C., R_f=0.33 (methylene chloride:methanol:25% aqueous ammonia solution=95:5:1).

The starting material N-(5-amino-2-methylphenyl)-4-(3-pyridyl)-2-pyrimidine-amine is obtained as follows:

9.1 ml (0.13 mol) of 65% nitric acid are added dropwise in the course of 5 minutes to a yellow suspension of 20.0 g (0.13 mol) of 2-amino-4-nitrotoluene in 50 ml of absolute ethanol. When the exothermic reaction has subsided, 8.32 g (0.198 mol) of cyanamide dissolved in 8.3 ml of water are added. The brown reaction mixture is boiled at reflux for 25 hours, cooled to 0.degree. and filtered. Washing with 4.times.100 ml of ethanol/diethyl ether (1:1) and drying yield 2-methyl-5-nitrophenyl-guanidine nitrate; m.p. 219° C.-226° C.

248.2 g (0.96 mol) of 2-methyl-5-nitrophenylguanidine nitrate are added to a solution of 170 g (0.96 mol) of 3-dimethylamino-1-(3-pyridyl)-2-propen-1-one in 2.0 liters of isopropanol. After the addition of 42.5 g of sodium hydroxide, the reddish suspension is boiled at reflux for 12 hours. After cooling to 0° C., filtration, washing with 2.0 liters of isopropanol and 3.times.400 ml of methanol and drying, there is obtained N-(2-methyl-5-nitrophenyl)-4-(3-pyridyl)-2-pyrimidine-amine, m.p. 195° C.-198° C., R_f=0.68 (methylene chloride:methanol=9.1).

A suspension of 143.0 g (0.46 mol) of N-(2-methyl-5-nitrophenyl)-4-(3-pyridyl)-2-pyrimidine-amine in 7.15 liters of ethyl acetate is stirred with 14.3 g of palladium on active carbon (10% Pd) under a hydrogen atmosphere at normal pressure for 6.5 hours. The suspension is filtered and the filtrate is concentrated in a rotary evaporator. The crude product is recrystallised from methylene chloride, yielding N-(5-amino-2-methylphenyl)-4-(3-pyridyl)-2-pyrimidine-amine; m.p. 138° C.-140° C., R_f=0.36 (methylene chloride:methanol=9:1).

Example 45

Preparation of a Pharmaceutical Formulation of Form V

Form V, having the main PXRD peaks at 9.9, 11.7, 13.3, 16.6, and 22.1±0.2 degrees two-theta, and all the components presented in the below table were weighed together and mixed to obtain a tablet.

| Colloidal silicon dioxide | 1 mg |
| Crosspovidone | 16 mg |
| Klucel | 9 mg |
| Magnesium stearate | 2 mg |
| Avicel | 86 mg |
| Imatinib mesylate substance | 86 mg |
| Total weight | 200 mg |

Then, the tablet was pressed and analyzed by PXRD providing the following main PXRD peaks: 9.9, 11.7, 13.3, 16.6, and 22.1±0.2, which belong to form V.

Example 46

Preparation of a Pharmaceutical Formulation of Form X

Form X, having the main PXRD peaks at 6.0, 8.6, 11.4, 14.2, and 18.3±0.2 degrees two-theta, and all the components presented in the below table were weighed together and mixed to obtain a tablet.

| Colloidal silicon dioxide | 1 mg |
| Crosspovidone | 16 mg |
| Klucel | 9 mg |
| Magnesium stearate | 2 mg |
| Avicel | 86 mg |
| Imatinib mesylate substance | 86 mg |
| Total weight | 200 mg |

Then, the tablet was pressed and analyzed by PXRD providing the following main PXRD peaks: 6.0, 8.6, 11.4, 14.2, and 18.3±0.2, which belong to form X.

Example 47

Preparation of a Pharmaceutical Formulation of Amorphous Imatinib Mesylate

Amorphous Imatinib mesylate and all the components presented in the below table were weighed together and mixed to obtain a tablet.

| Colloidal silicon dioxide | 1 mg |
| Crosspovidone | 16 mg |
| Klucel | 9 mg |
| Magnesium stearate | 2 mg |
| Avicel | 86 mg |
| Imatinib mesylate substance | 86 mg |
| Total weight | 200 mg |

Then, the tablet was pressed and analyzed by PXRD showing no diffraction peaks, thus retaining the amorphous form.

What is claimed is:

1. A crystalline form of imatinib mesylate characterised by data selected from the group consisting of: a powder XRD pattern with peaks at 6.0, 8.6, 11.4, 14.2 and 18.3±0.2 degrees two-theta; a powder XRD pattern having peaks at 6.0, 8.6, 10.2, 11.4 and 14.2±0.2 degrees two-theta; a powder XRD pattern having at least five peaks selected from the list consisting of 6.0, 8.6, 10.2, 11.4, 14.2, 17.8, 18.3, 21.6, 22.4, 23.6 and 24.8±0.2 degrees two-theta; a powder XRD pattern as depicted in FIG. 19; a solid-state $^{13}$C NMR spectrum with signals at 159.9, 158.2 and 153.4±0.2 ppm; a solid-state $^{13}$C NMR spectrum having chemical shift differences between the signal exhibiting the lowest chemical shift and another in the chemical shift range of 100 to 180 ppm of 51.5, 49.8, and 45.0±0.1 ppm; a solid-state $^{13}$C NMR spectrum as depicted in FIG. 20; and a solid-state $^{13}$C NMR spectrum as depicted in FIG. 21.

2. Crystalline imatinib mesylate of claim 1, wherein the crystalline form is characterised by a powder XRD pattern with peaks at 6.0, 8.6, 11.4, 14.2 and 18.3±0.2 degrees two-theta.

3. Crystalline imatinib mesylate of claim 1, wherein the crystalline form is characterised by a powder XRD pattern having peaks at 6.0, 8.6, 10.2, 11.4 and 14.2±0.2 degrees two-theta.

4. Crystalline imatinib mesylate of claim 1, wherein the crystalline form is characterised by a powder XRD pattern having at least five peaks selected from the list consisting of 6.0, 8.6, 10.2, 11.4, 14.2, 17.8, 18.3, 21.6, 22.4, 23.6 and 24.8±0.2 degrees two-theta.

5. Crystalline imatinib mesylate of claim 1, wherein the crystalline form is characterised by a powder XRD pattern as depicted in FIG. 19.

6. Crystalline imatinib mesylate of claim 1, wherein the crystalline form is characterised by a solid-state $^{13}$C NMR spectrum with peaks at 159.9, 158.2 and 153.4±0.2 ppm.

7. Crystalline imatinib mesylate of claim 1, wherein the crystalline form is characterised by a solid-state $^{13}$C NMR spectrum having chemical shift differences between the signal exhibiting the lowest chemical shift and another in the chemical shift range of 100 to 180 ppm of 51.5, 49.8, and 45.0±0.1 ppm.

8. Crystalline imatinib mesylate of claim 1, wherein the crystalline form is characterised by a solid-state $^{13}$C NMR spectrum as depicted in FIG. 20.

9. Crystalline imatinib mesylate of claim 1, wherein the crystalline form is characterised by a solid-state $^{13}$C NMR spectrum as depicted in FIG. 21.

10. Crystalline imatinib mesylate of claim 1, wherein the crystalline form is further characterised by a powder XRD pattern having peaks at 19.9, 20.5, 21.6 and 22.4±0.2 degrees two-theta.

11. Crystalline imatinib mesylate of claim 2, wherein the crystalline form is further characterised by a powder XRD pattern having peaks at 10.2, 20.5 and 21.6±0.2 degrees two-theta.

12. Crystalline imatinib mesylate of claim 6, wherein the crystalline form is further characterised by a solid-state $^{13}$C NMR spectrum having signals at 146.2 and 140.6±0.2 ppm.

13. Crystalline imatinib mesylate of claim 7, wherein the crystalline form is further characterised by a solid-state $^{13}$C NMR spectrum having chemical shift differences between the signal exhibiting the lowest chemical shift and another in the chemical shift range of 100 to 180 ppm of 37.8 and 32.2±0.1 ppm.

14. Crystalline imatinib mesylate of claim 12, wherein the crystalline form is further characterized by a solid-state $^{13}$C NMR spectrum having signals at 19.4 and 17.7±0.1 ppm.

15. Crystalline imatinib mesylate of claim 1, wherein the crystalline form is an ethanol solvate of imatinib mesylate.

16. A process for preparing crystalline imatinib mesylate according to claim 1, said process comprising: maintaining a crystalline imatinib mesylate solvate at a temperature of about 20° C. to about 30° C.; wherein said crystalline solvate is a tetrahydrofuran or dioxolane solvate of Imatinib mesylate.

17. A process for preparing crystalline imatinib mesylate according to claim 1, said process comprising:
a) providing a solution of imatinib mesylate in a mixture of water and ethanol; and
b) precipitating imatinib mesylate by maintaining the solution at a temperature of about −5° C. to about −30° C.

18. The process of claim 17, wherein the solution of imatinib mesylate in a mixture of water and ethanol is provided by:
a) combining imatinib base with ethanol to form a first suspension;
b) adding water to the first suspension to obtain a second suspension;
c) cooling the second suspension; and
d) adding methanesulfonic acid to the cooled second suspension.

19. The process of claim 18, wherein the second suspension is cooled in step c) to a temperature of about −30° C. to about 0° C.

20. The process of claim 17, wherein precipitating in step b) comprises a first cooling of the solution at a temperature of about −10° C. to about 0° C., and a second further cooling to a temperature of about −30° C. to about −15° C.

21. A process for preparing crystalline imatinib mesylate according to claim 1, said process comprising suspending in ethanol, a crystalline form of imatinib mesylate characterized by data selected from the group consisting of: a powder XRD pattern with peaks at 9.9, 11.7, 13.3, 16.6 and 22.1±0.2 degrees two-theta; a powder XRD pattern with peaks at 9.9, 11.7, 13.3 and 16.6±0.2 degrees two-theta; a powder XRD pattern having peaks at 5.6, 9.9, 11.7, 13.3, 16.6 and 18.5±0.2 degrees two-theta; a powder XRD pattern having at least five peaks selected from 5.6, 9.9, 11.7, 13.3, 16.6, 18.5, 22.1, 24.0, 26.2 and 26.9±0.2 degrees two-theta; a powder XRD pattern as depicted in the FIG. 4; a solid-state $^{13}$C NMR spectrum with peaks at 162.8, 161.5 and 158.5±0.2 ppm; a solid-state $^{13}$C NMR spectrum having chemical shift differences between the signal exhibiting the lowest chemical shift and another in the chemical shift range of 100 to 180 ppm of 53.9, 52.6 and 49.6±0.1 ppm, a solid state $^{13}$C NMR as depicted in FIG. 5, and a solid state $^{13}$C NMR spectrum as depicted in FIG. 6.

22. A pharmaceutical composition comprising the crystalline form of imatinib mesylate according to claim 1, and at least one pharmaceutically acceptable excipient.

23. A pharmaceutical composition comprising a crystalline form of imatinib mesylate made according to the process of any one of claims 16 to 21, and at least one pharmaceutically acceptable excipient.

* * * * *